(12) United States Patent
Lin et al.

(10) Patent No.: US 8,703,882 B2
(45) Date of Patent: Apr. 22, 2014

(54) PHOSPHORUS-CONTAINING BENZOXAZINE-BASED BISPHENOLS, DERIVATIVES THEREOF, AND PREPARING METHOD FOR THE SAME

(75) Inventors: Ching-Hsuan Lin, Taichung (TW); Hung-Tse Lin, Changhua (TW); Sheng Lung Chang, Dayuan Township, Taoyuan County (TW); Yu-Ming Hu, Shanhua Township, Tainan County (TW)

(73) Assignee: National Chunghsing University, Taichung (TW)

( * ) Notice: Subject to any disclaimer, the term of this patent is extended or adjusted under 35 U.S.C. 154(b) by 290 days.

(21) Appl. No.: 12/979,394

(22) Filed: Dec. 28, 2010

(65) Prior Publication Data
US 2011/0257347 A1    Oct. 20, 2011

(30) Foreign Application Priority Data
Dec. 31, 2009  (TW) ............................... 98146518 A

(51) Int. Cl.
C07D 327/04    (2006.01)
C07F 9/655     (2006.01)
C08G 59/30     (2006.01)
C08L 63/00     (2006.01)
C08L 63/02     (2006.01)

(52) U.S. Cl.
USPC ............. 525/481; 525/523; 525/533; 528/96; 548/413; 549/7; 549/218; 549/219; 558/76

(58) Field of Classification Search
None
See application file for complete search history.

(56) References Cited

U.S. PATENT DOCUMENTS

| | | | |
|---|---|---|---|
| 8,058,362 B2 * | 11/2011 | Lin et al. | 525/505 |
| 2006/0149023 A1 * | 7/2006 | Wang et al. | 528/167 |
| 2007/0129509 A1 | 6/2007 | Li et al. | |
| 2009/0171120 A1 | 7/2009 | Lin et al. | |
| 2009/0215967 A1 | 8/2009 | Lin et al. | |
| 2009/0274916 A1 * | 11/2009 | Takahashi et al. | 428/457 |
| 2009/0280331 A1 * | 11/2009 | Takahashi et al. | 428/416 |

FOREIGN PATENT DOCUMENTS

| JP | 2004217886 A | 8/2004 |
|---|---|---|
| TW | 528769 | 4/2003 |

OTHER PUBLICATIONS

Lin et al., "Approach to Develop High-Tg Epoxy Resins for Halogen-Free Copper Clad Laminates," PMSE Preprints, American Chemical Society, 2010, two pages.*

* cited by examiner

*Primary Examiner* — Robert Sellers
(74) *Attorney, Agent, or Firm* — CKC & Partners Co., Ltd.

(57) ABSTRACT

Phosphorus-containing benzoxazine-based bisphenols and derivatives thereof are disclosed. The phosphorus-containing benzoxazine-based bisphenols are prepared by reacting DOPO with benzoxazine to form the phosphorus-containing benzoxazine-based bisphenols. The phosphorus-containing benzoxazine-based bisphenols can further to form advanced epoxy resins. The advanced epoxy resins can further be cured to form flame retardant epoxy thermosets.

19 Claims, 3 Drawing Sheets

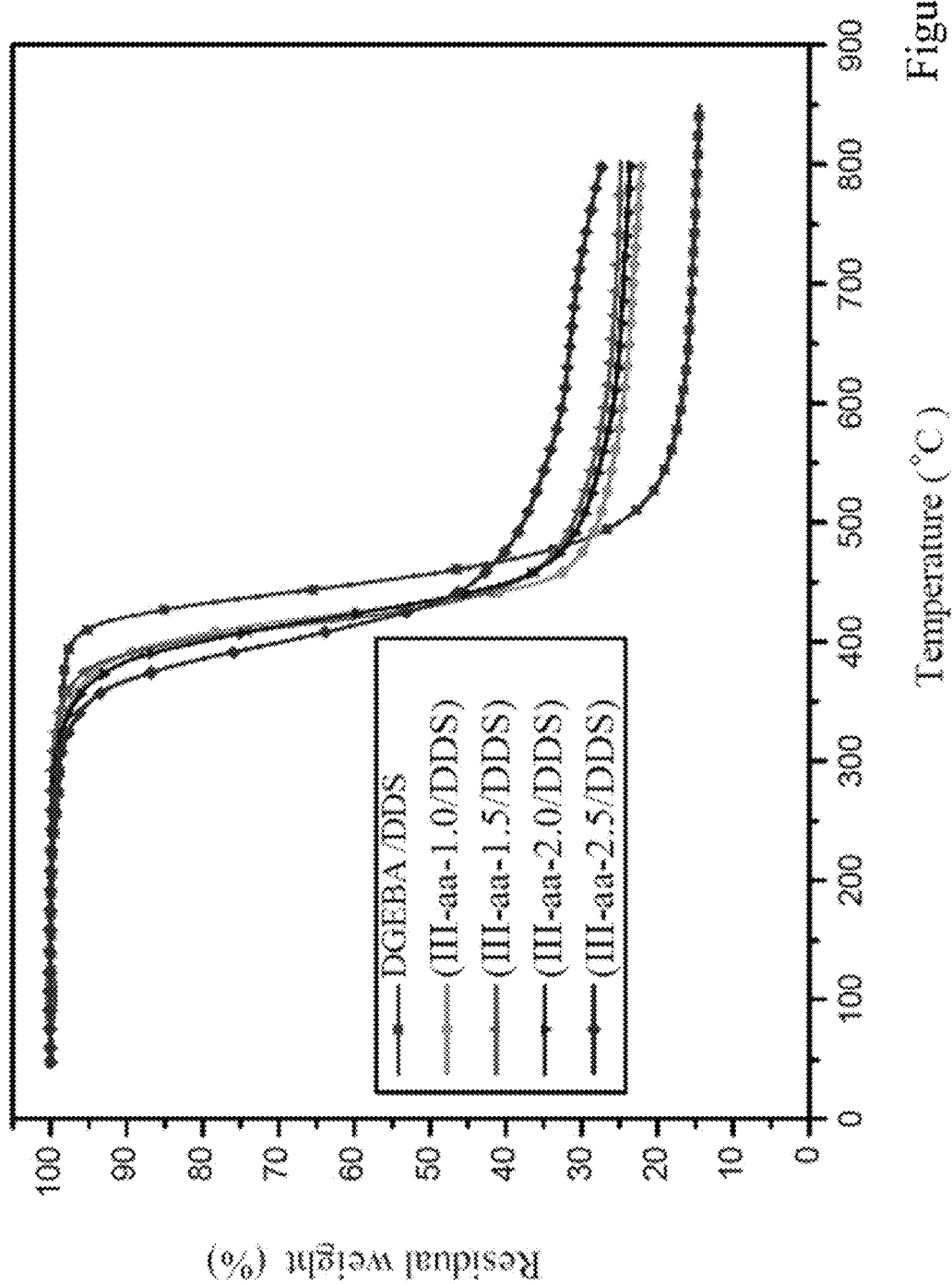

PHOSPHORUS-CONTAINING BENZOXAZINE-BASED BISPHENOLS, DERIVATIVES THEREOF, AND PREPARING METHOD FOR THE SAME

BACKGROUND

1. Field of Disclosure

The present disclosure relates to a phosphorus-containing bisphenol, derivative thereof and preparing method for the same. More particularly, the present disclosure relates to a phosphorus-containing benzoxazine-based bisphenol and preparing method thereof.

2. Description of Related Art

Currently, among the epoxy resins applied in a printed circuit board, halogen and antimony trioxide are main flame retardant additives. For example, halogen-containing tetrabromobisphenol is the most widely used flame retardant epoxy resin.

However, when burning, a halogen-containing flame retardant epoxy thermoset may not only produce a corrosive gas but also produce a noxious carcinogenic gas, such as dioxin, benzofuran and the like. Therefore, the main development direction of the flame retardant is to replace halogen with other elements to form a new halogen-free flame retardant.

Currently, among the flame retardant epoxy resins applied in the printed circuit board, a phosphorus-containing epoxy resin material derived from phosphorus-containing bisphenol DOPOBQ and DOPONQ has a better property and reliability. However, there are still some problems in using the above phosphorus-containing epoxy resin material. For example, its poor solubility makes it soluble only in a solvent with a high boiling point, which increases the manufacturing cost and also restricts its industrial application.

SUMMARY

An aspect of the present disclosure provides a series of phosphorus-containing bisphenols and preparing method thereof, wherein the phosphorus-containing bisphenols are prepared by reacting a benzoxazine monomer with a phosphorus-containing compound, DOPO. The present disclosure includes a ring-opening reaction of the benzoxazine monomer with the DOPO to form a phosphorus-containing bisphenol. The benzoxazine monomer includes an aromatic diamine-based benzoxazine monomer or a bisphenol-based benzoxazine monomer.

According to an embodiment of the present disclosure, a phosphorus-containing bisphenol (I) is prepared by reacting an aromatic diamine-based benzoxazine monomer with a phosphorus-containing compound, DOPO, and has a general formula shown as follows:

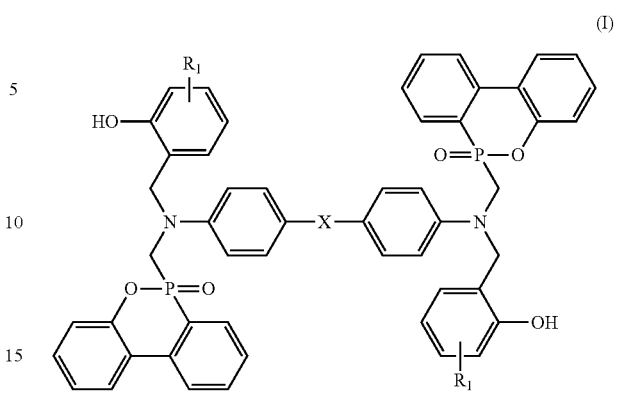

(I)

According to another embodiment of the present disclosure, a phosphorus-containing bisphenol (II) is prepared by reacting a bisphenol-based benzoxazine monomer with a phosphorus-containing compound, DOPO, and has a general formula shown as follows:

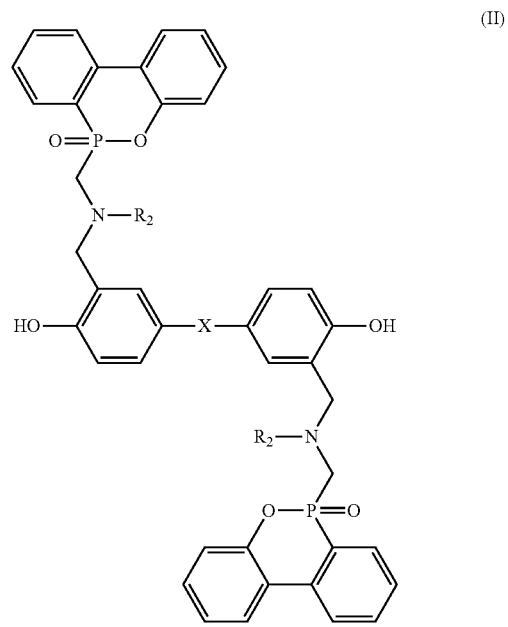

(II)

wherein, $R_1$ is selected from the following groups:

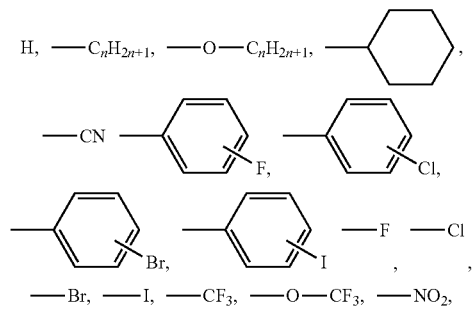

-continued
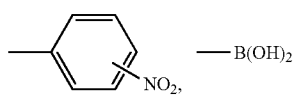
$R_2$ is selected from the following groups:
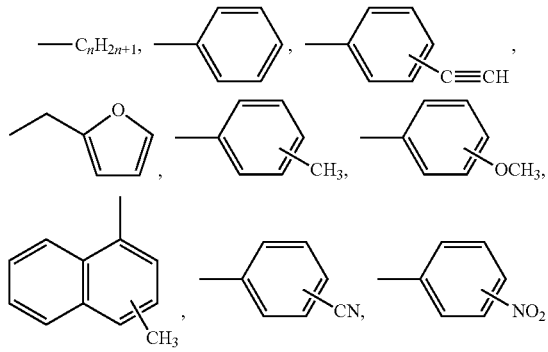
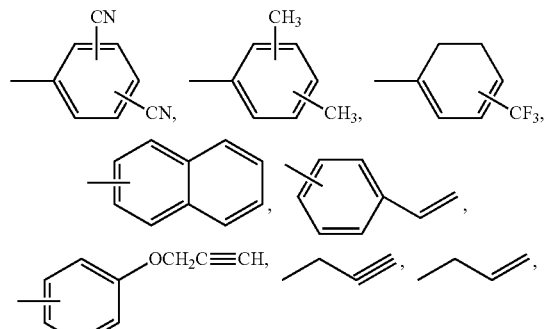
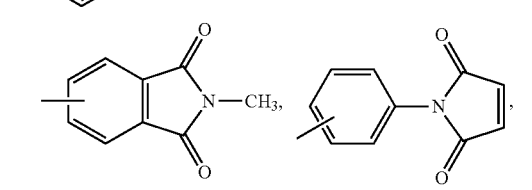
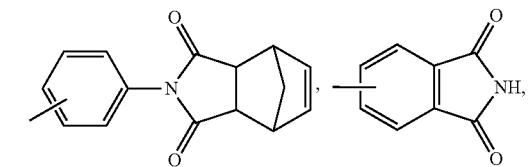
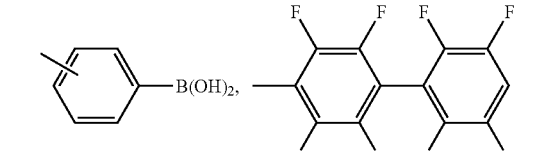
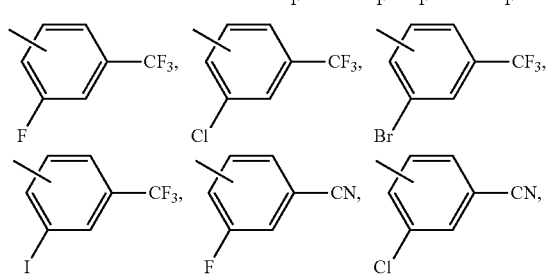
-continued
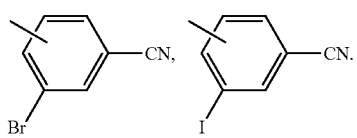
and X includes the following structures:
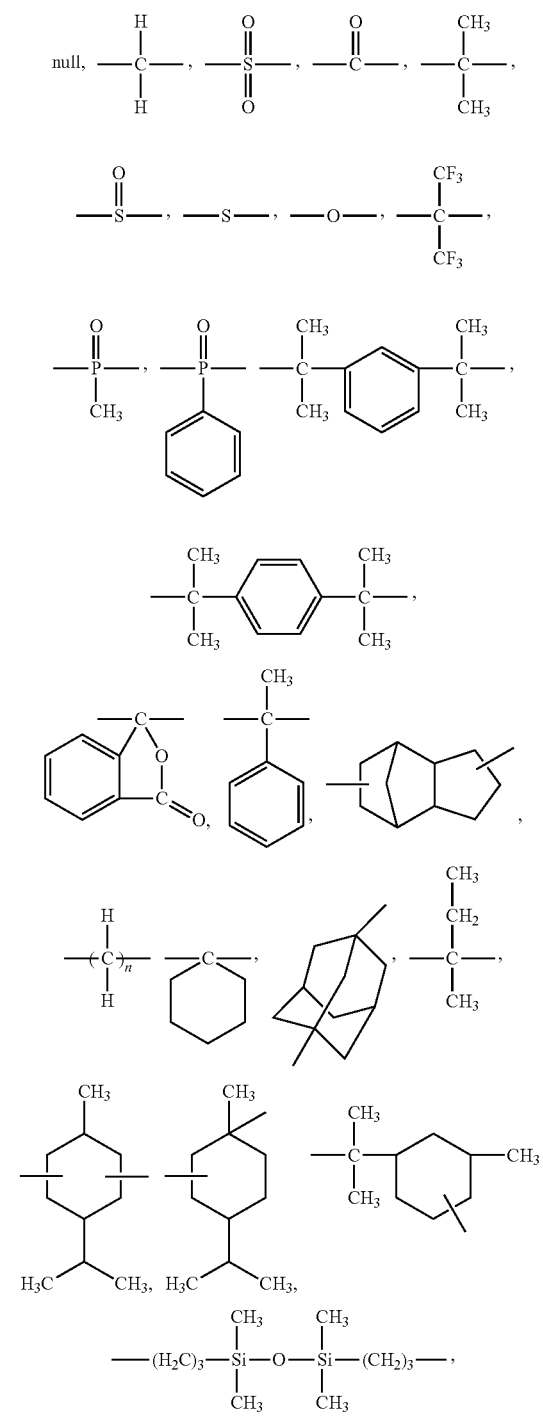

-continued

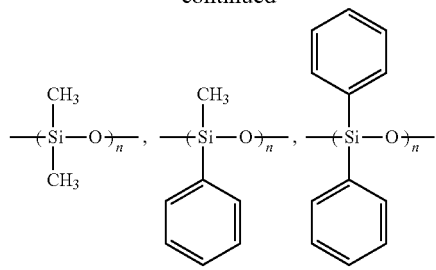

wherein, n is an integer which is equal to or greater than 1 but less than or equal to 10.

According to an embodiment of the present disclosure, an advanced phosphorus-containing flame retardant epoxy resin (III) derived from the phosphorus-containing bisphenols (I) has a general formula shown as follows:

Another aspect of the present disclosure provides a method of preparing a phosphorus-containing flame retardant epoxy resin, which includes following steps. The phosphorus-containing bisphenol (I) or (II) is reacted with a compound (C) having an epoxy group for a chain extension reaction without a catalyst or with few catalysts by heating, so as to form an advanced phosphorus-containing flame retardant epoxy resin. The advanced phosphorus-containing flame retardant epoxy resin can further be cured to form a phosphorus-containing flame retardant epoxy thermoset.

The compound (C) has a structure as shown in the following formula:

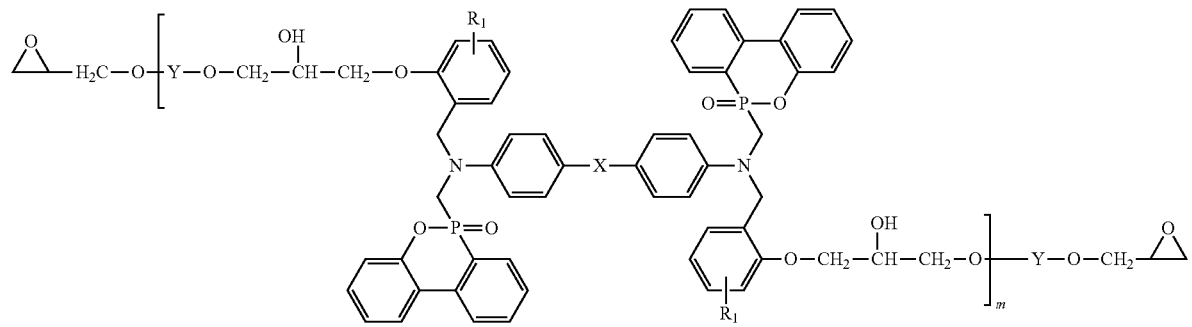

(III)

According to another embodiment of the present disclosure, an advanced phosphorus-containing flame retardant epoxy resin (IV) derived from the phosphorus-containing bisphenol (II) has a structure as shown in the following formula:

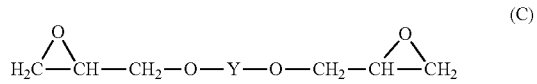

(C)

Y is selected from the following groups:

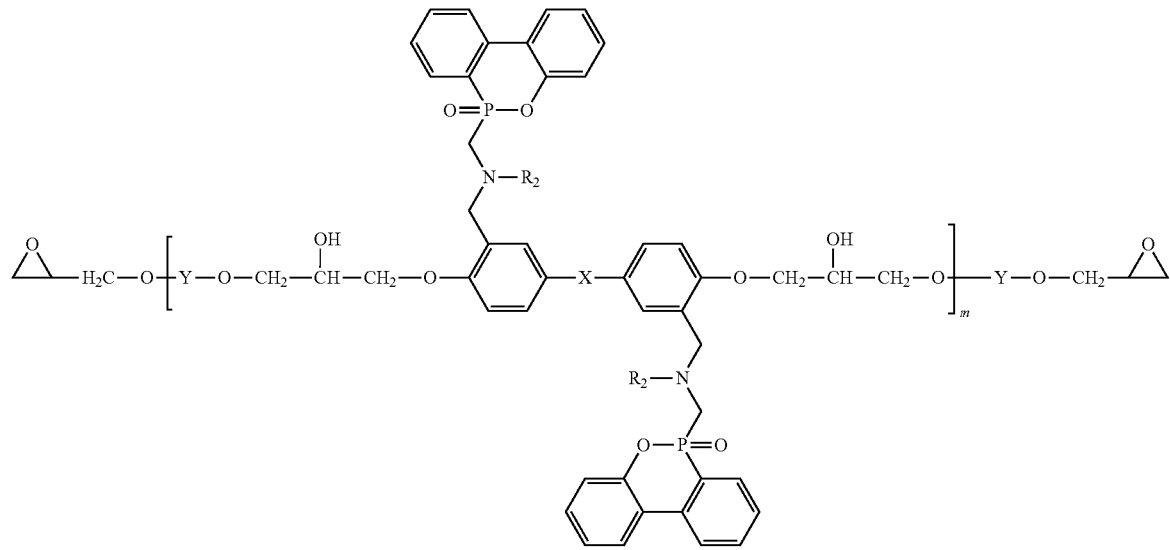

-continued wherein, m is a number which is equal to or greater than 1 but less than or equal to 10, and T and Q are respectively selected from a group consisting of: hydrogen, $C_1$-$C_6$ alkyl, $CF_3$, phenyl and halogen.

In view of the above, the embodiments of the present disclosure have the following technical advantages:

1. The embodiments of the present disclosure provide a novel manner of synthesizing phosphorus-containing bisphenols. The phosphorus-containing compound DOPO is successfully introduced into a benzoxazine monomer, to form a highly active phosphorus-containing bisphenol, thereby improving a flame resistance of a benzoxazine resin.

2. The phosphorus-containing bisphenol synthesized according to the embodiments of the present disclosure can be reacted with an epoxy resin for an advancement reaction, to form an advanced phosphorus-containing flame retardant epoxy resin without adding a catalyst during the synthetic process, and thus the synthetic steps are simple. Moreover, the advanced phosphorus-containing flame retardant epoxy resin has the properties of an excellent solubility and a low viscosity and has the advantages of convenient processing and mass production.

3. A thermoset of the advanced phosphorus-containing flame retardant epoxy resin in the embodiments of the present disclosure has a good flame resistance and a thermal stability.

BRIEF DESCRIPTION OF THE DRAWINGS

In order to make the following as well as other aspects, features, advantages, and embodiments of the present disclosure more apparent, the accompanying drawings are described as follows:

FIG. 3 is a thermogravimetric analysis diagram of a series of (III-aa)/DDS thermosets with different phosphorus contents.

DETAILED DESCRIPTION

Figure 1:
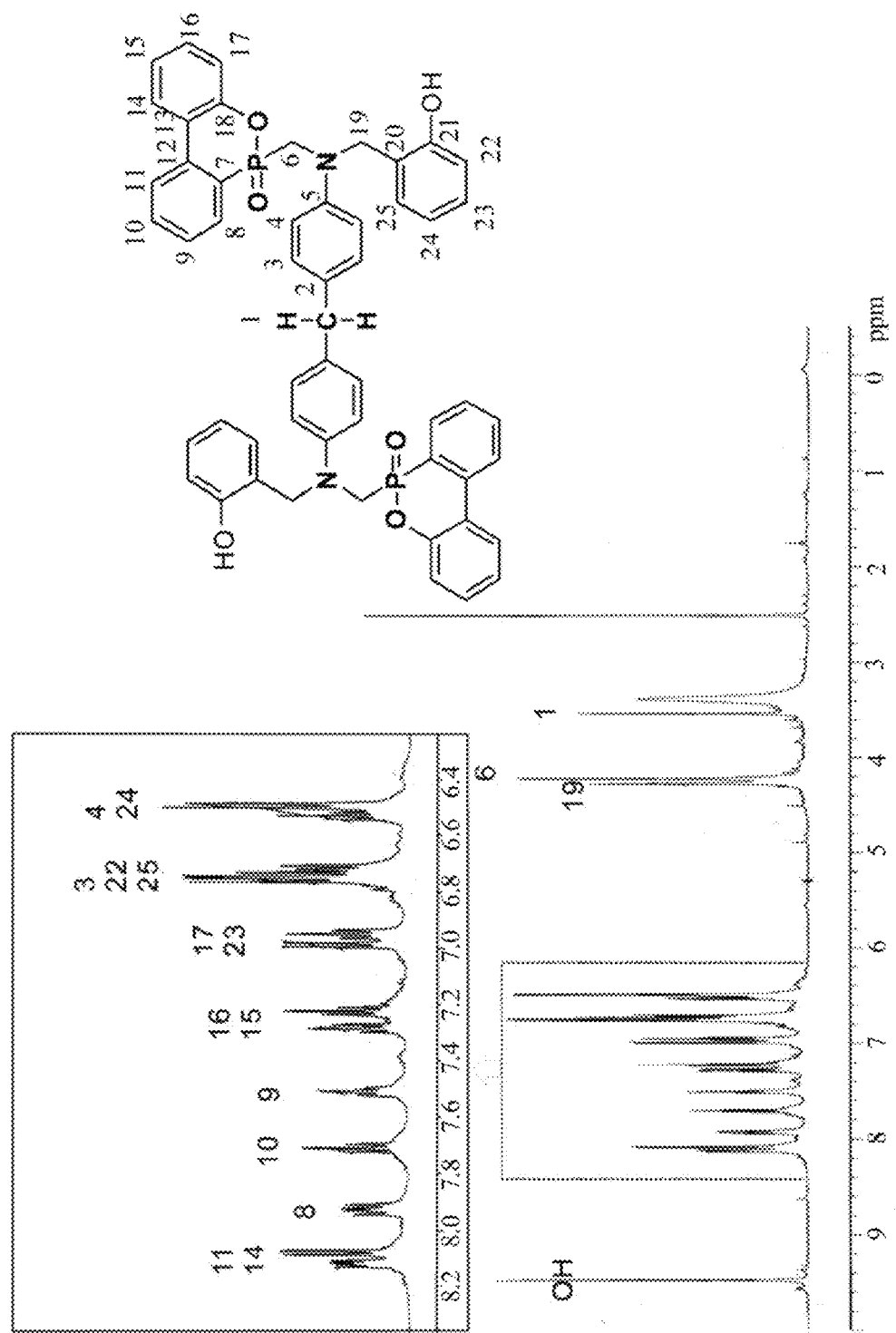
FIG. 1 is a $^1$H NMR spectrum of a phosphorus-containing bisphenol (I-a) according to an embodiment of the present disclosure.

The present disclosure provides a series of phosphorus-containing bisphenols, derivatives thereof and preparing method for the same. The phosphorus-containing bisphenols are prepared by a ring-opening reaction of DOPO, a phosphorus-containing compound, with a benzoxazine monomer having a bifunctional group.

DOPO (9,10-dihydro-9-oxa-10-phosphaphenanthrene 10-oxide) is a phosphorus-containing compound, which has an active hydrogen atom and thus can be reacted with an electron-defect compound. Benzoxazine is a compound having a structure in which a benzene ring is linked to a heterocyclic ring containing nitrogen and oxygen, and the heterocyclic ring containing nitrogen and oxygen can be polymerized to form a high polymer through a ring-opening reaction during heating. The benzoxazine monomer used in the embodiments of the present disclosure is a benzoxazine monomer with a bifunctional group, which is generally formed by condensation and ring closure of bisphenol or aromatic diamine with aldehyde and, aniline. However, the present disclosure is not limited to the above method.

According to an embodiment of the present disclosure, a phosphorus-containing bisphenol (I) is prepared by mixing the phosphorus-containing compound DOPO with a benzoxazine monomer (A) in a solution and conducting a ring-opening reaction of the benzoxazine (A) through heating.

According to another embodiment of the present disclosure, a phosphorus-containing bisphenols (II) is synthesized by means of the above method, which differs in the replacement of the benzoxazine monomer (A) with a benzoxazine monomer (B), for a ring-opening reaction of the benzoxazine (B) with the phosphorus-containing compound (DOPO).

The structures of the phosphorus-containing compound (DOPO), benzoxazine monomer (A) and benzoxazine monomer (B) are respectively shown as follows:

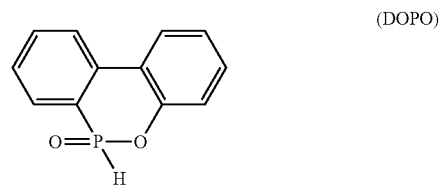

(DOPO)

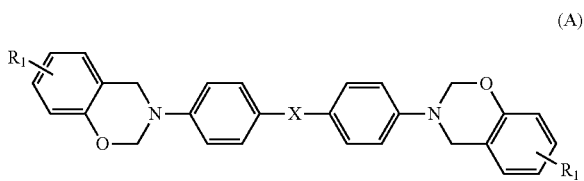

(A)

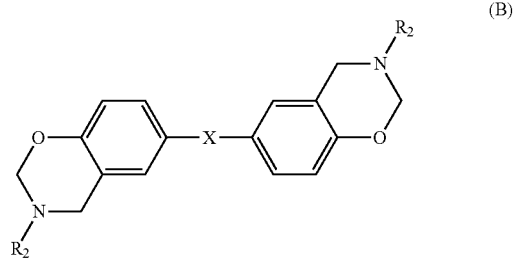

(B)

According to the embodiments of the present disclosure, the above phosphorus-containing bisphenols (I) and (II) can further be reacted with a compound (C) with an epoxy group for a chain extension reaction, so as to form advanced phosphorus-containing flame retardant epoxy resins (III) and (IV), wherein the compound (C) has a structure as shown in the following formula:

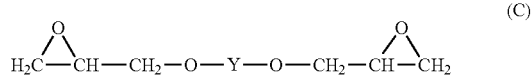

(C)

The phosphorus-containing flame retardant epoxy resins (III) and (IV) respectively have the following structures:

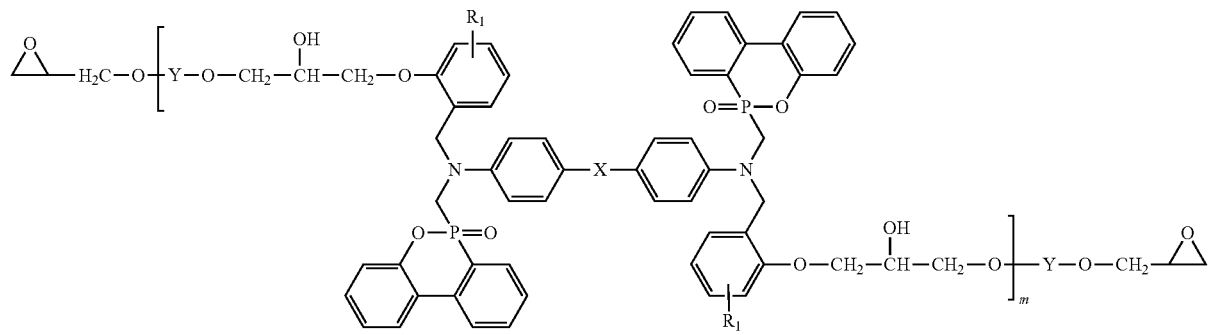

(III)

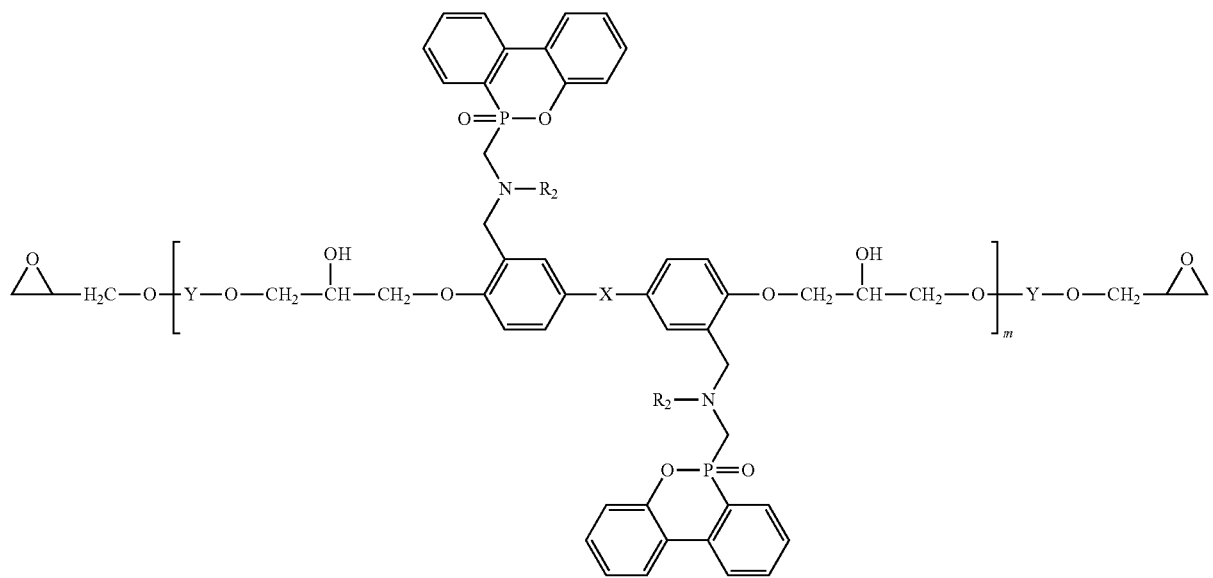

(IV)

According to the embodiments of the present disclosure, after the advanced Phosphorus-containing flame retardant epoxy resin (III) or (IV) is reacted with a curing agent, a flame retardant epoxy thermoset can be formed.

Embodiment 1

Synthesis of the Phosphorus-Containing Bisphenol (I)

According to the embodiments of the present disclosure, the phosphorus-containing bisphenol (I) can be synthesized by mixing DOPO with the to benzoxazine monomer (A) in a solution and then heating them, and the equation is shown as follows:

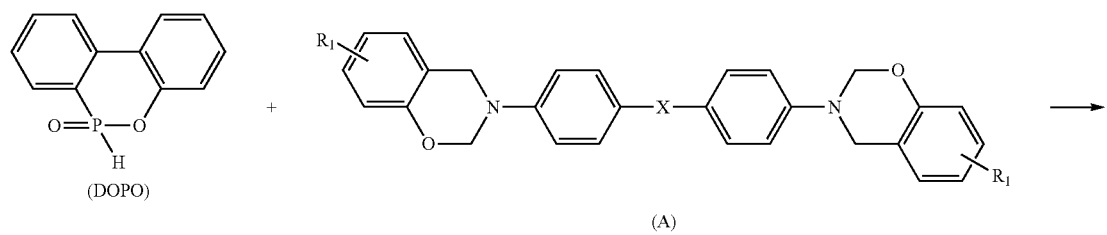

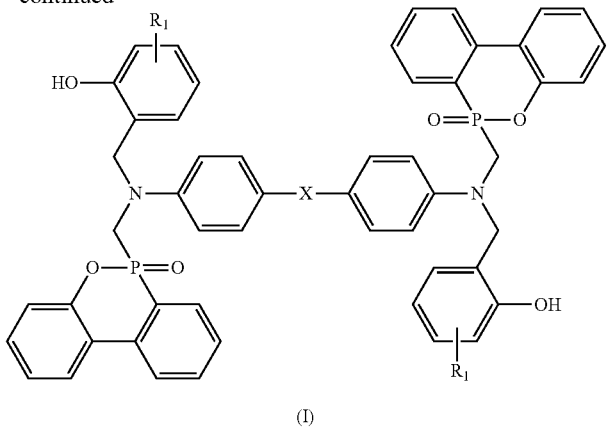

(I)

wherein, $R_1$ is selected from the following groups:

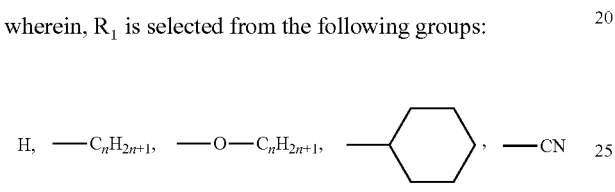

and X includes the structures shown as follows:

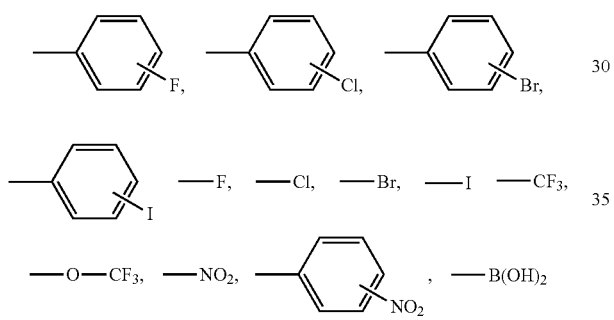

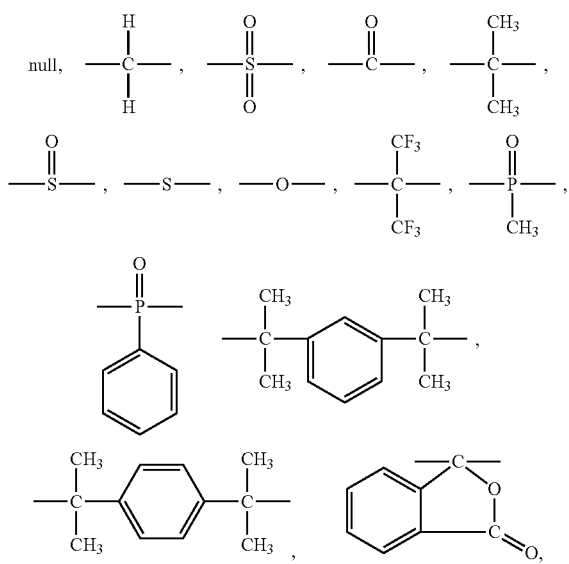

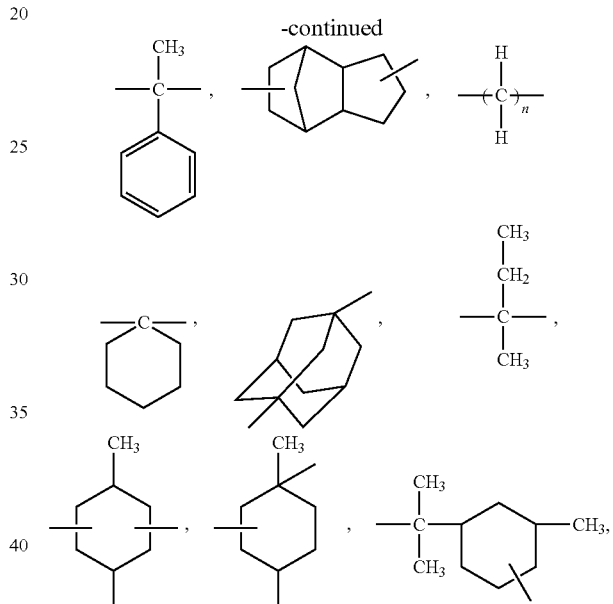

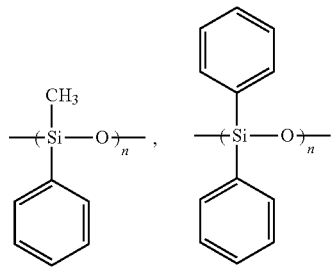

wherein, n is an integer which is equal to or greater than 1 but less than or equal to 10.

Advanced Phosphorus-Containing Flame Retardant Epoxy Resin (III) Derived from the Phosphorus-Containing Bisphenol (I):

The phosphorus-containing bisphenol (I) can further be reacted with a compound with an epoxy group for a chain extension reaction, to form the advanced phosphorus-containing flame retardant epoxy resin (III). The compound with an epoxy group may be any suitable epoxy resin, for example, a bifunctional epoxy compound such as bisphenol A resin, bisphenol F resin, bisphenol S resin, biphenol resin and the like.

According to an embodiment of the present disclosure, an epoxy resin with the structure of the compound (C) can be reacted with the phosphorus-containing bisphenol (I) at 100-200° C. for a chain extension reaction, to form the advanced phosphorus-containing flame retardant epoxy resin (III), and the reaction is shown as follows:

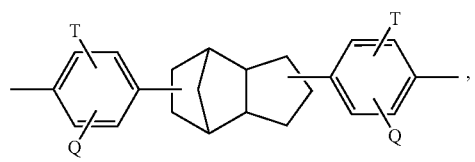

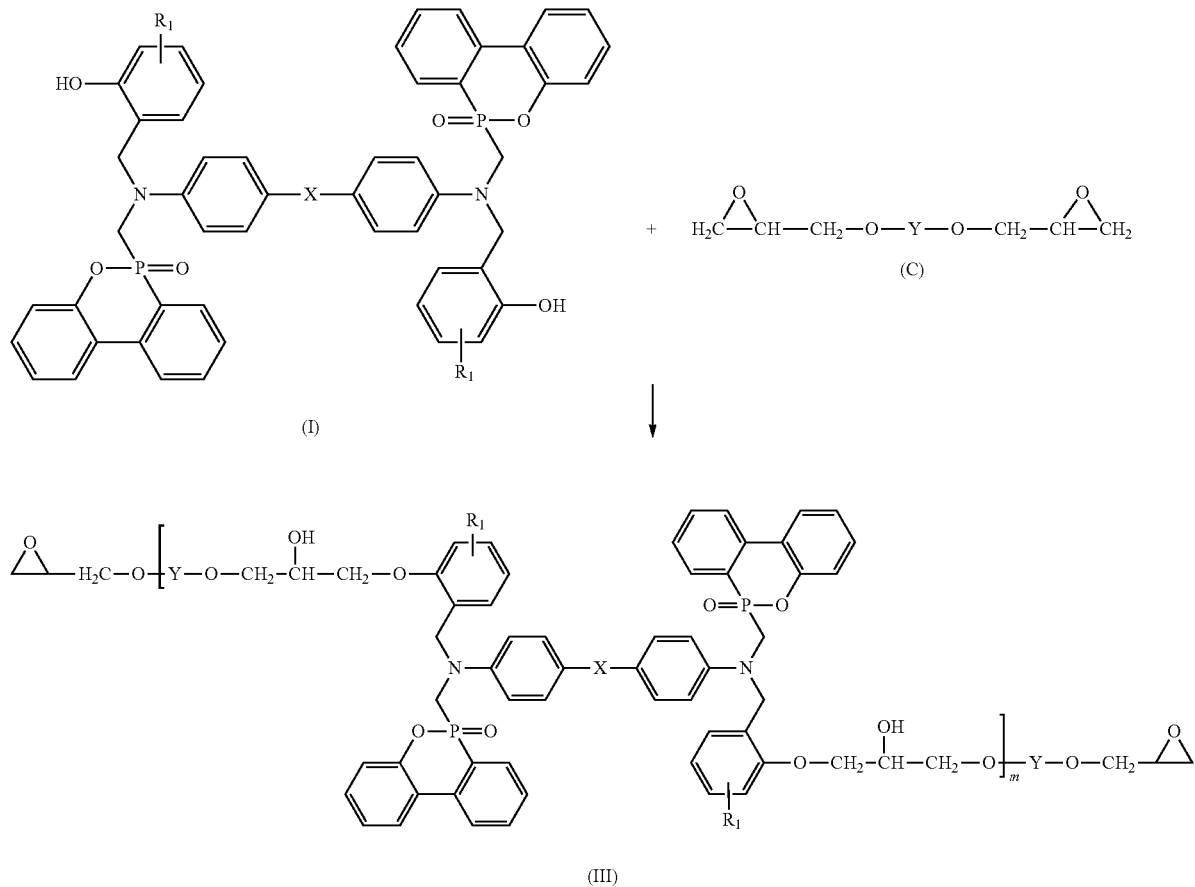

wherein, m is a number which is equal to or greater than 1 but less than or equal to 10, and Y is selected from the following groups:

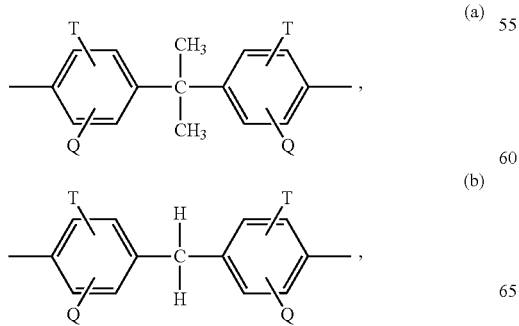

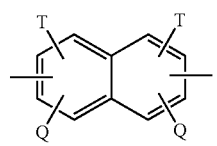

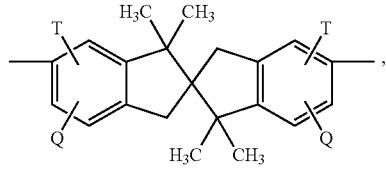

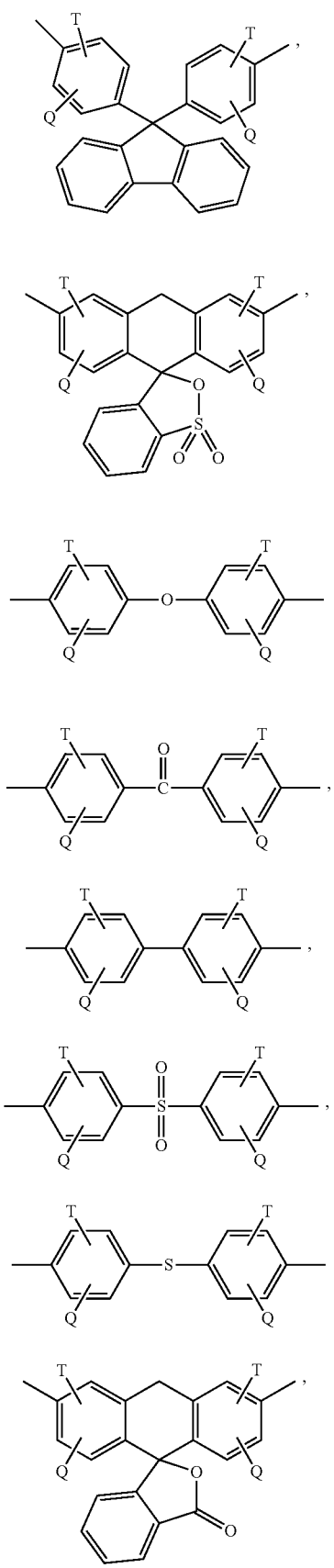

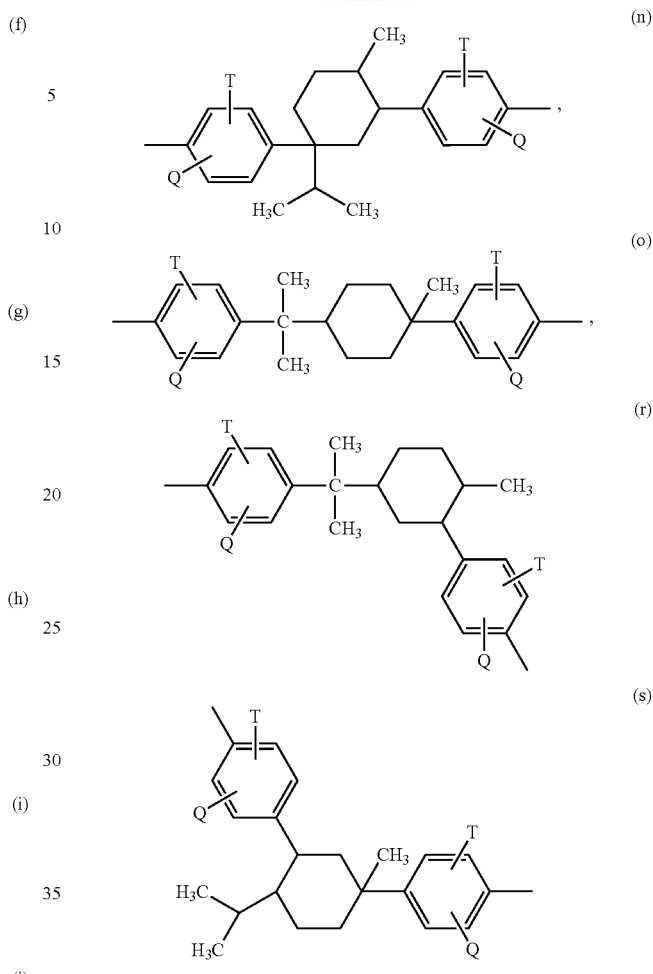

wherein, T and Q are respectively selected from a group consisting of hydrogen, $C_1$-$C_6$ alkyl, $CF_3$, phenyl and halogen.

According to one or more embodiments of the present disclosure, a phosphorus content of the advanced phosphorus-containing flame retardant epoxy resin (III) is 0.54 wt %.

According to one or more embodiments of the present disclosure, a ratio of an epoxy group equivalent in the compound (C) to a phenolic equivalent in the phosphorus-containing bisphenol (I) is between 1:1 and 10:1.

According to this embodiment, a chain extension reaction can be carried out without a catalyst. However, the reaction can also be carried out with few catalysts, which can accelerate the reaction. The catalyst may be phenylimidazole, dimethylmidazole, triphenylphosphine, quaternary phosphorus compound and quaternary ammonium compound.

Curing of the Advanced Phosphorus-Containing Flame Retardant Epoxy Resin (III):

The advanced phosphorus-containing flame retardant epoxy resin (III) can be cured through a curing agent, to form a phosphorus-containing flame retardant epoxy thermoset.

According to the embodiments of the present disclosure, the curing agent may be phenol novolac resin, dicyandiamide, diaminodiphenyl methane, diaminodiphenyl sulfone, phthalic anhydride or hexahydrophthalic anhydride.

Embodiment 2

Phosphorus-Containing Bisphenol (II)

According to this embodiment, phosphorus-containing bisphenol (II) can be synthesized by mixing the benzoxazine monomer (B) with DOPO in a solution and then heating them, and the equation is shown as follows:

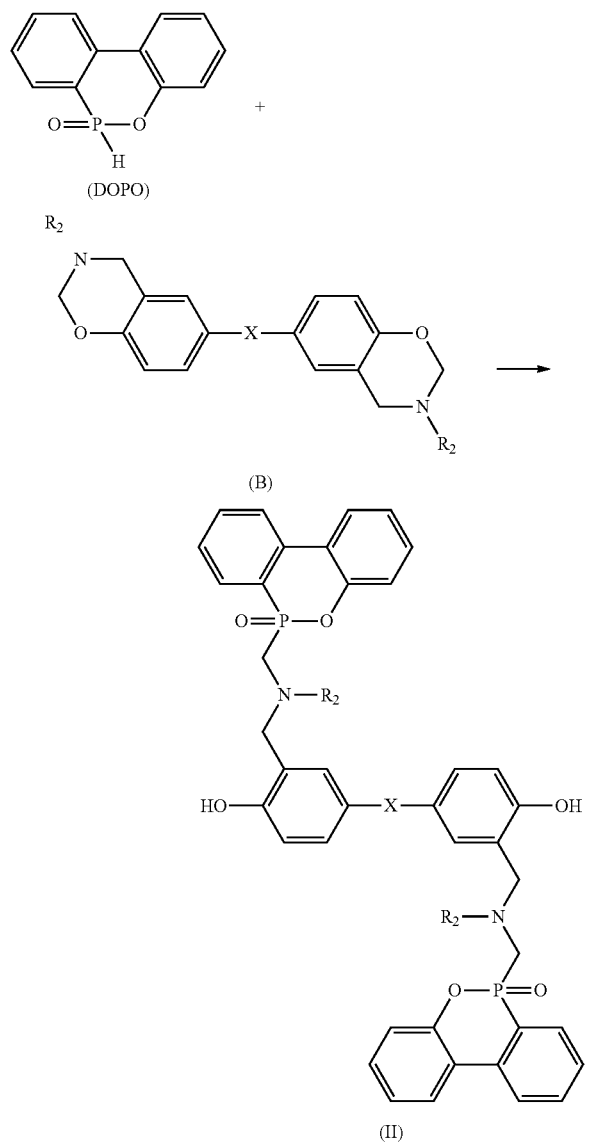

wherein, $R_2$ is selected from the following groups:

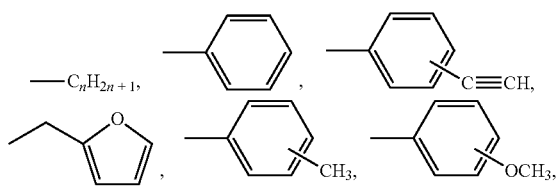

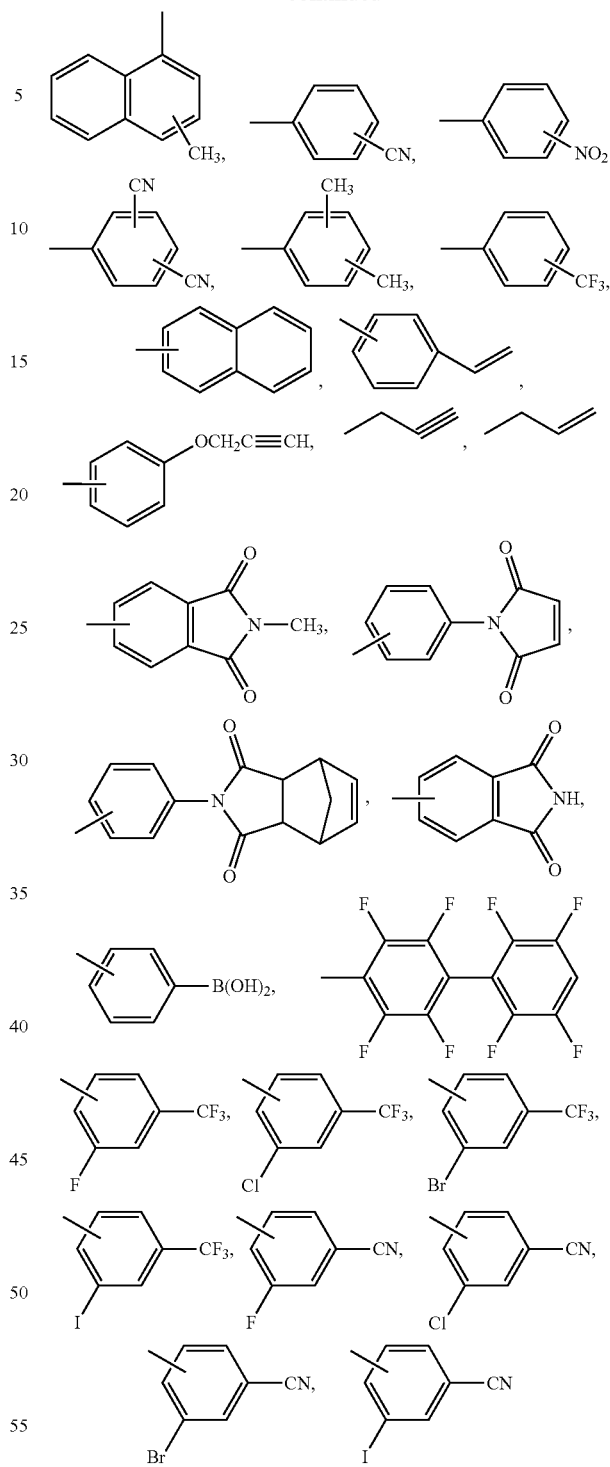

and X includes but is not limited to the structures shown as follows:

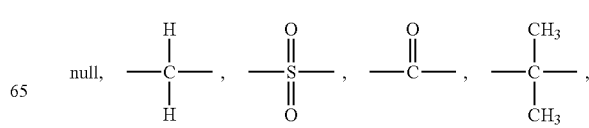

-continued

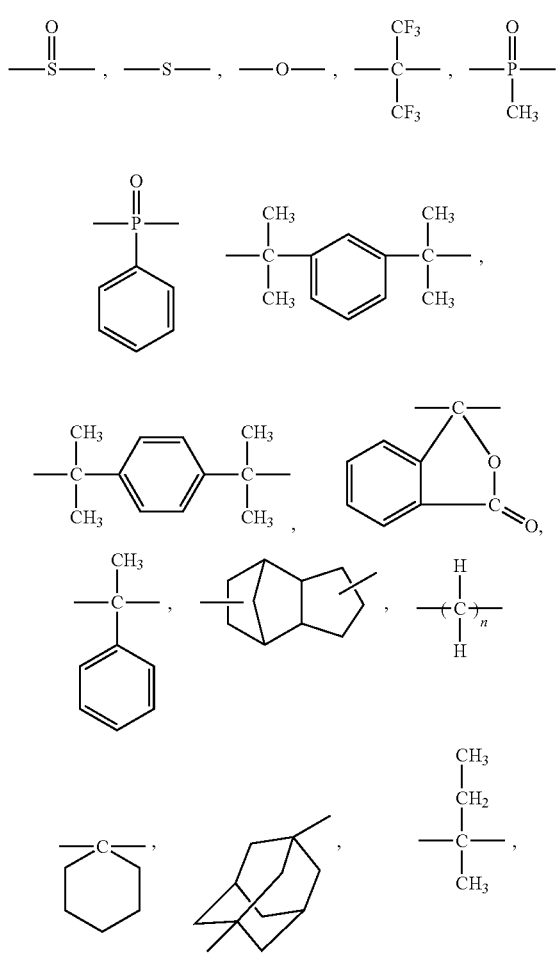

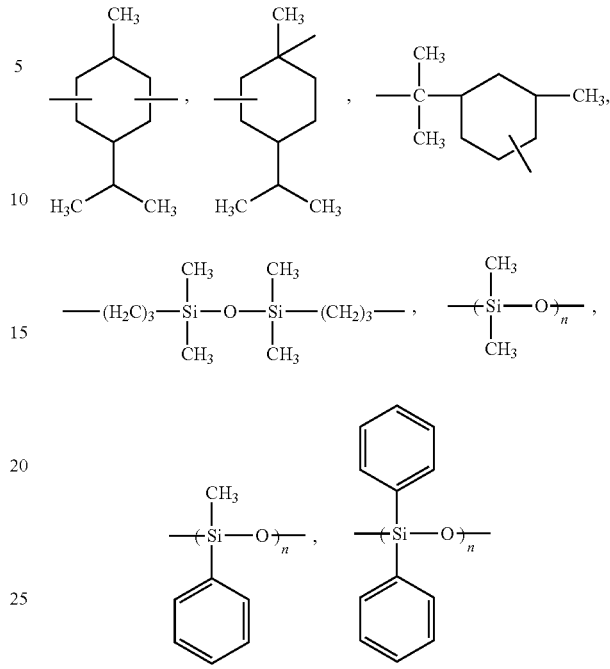

wherein, n is an integer which is equal to or greater than 1 but less than or equal to 10.

Advanced Phosphorus-Containing Flame Retardant Epoxy Resin (IV) Synthesized Through the Phosphorus-Containing Bisphenol (II):

By means of the same method in embodiment 1, the phosphorus-containing bisphenol (II) can be reacted with the compound (C) with an epoxy group at 100-200° C. for a chain extension reaction, to form the advanced phosphorus-containing flame retardant epoxy resin (IV), and the reaction is shown as follows:

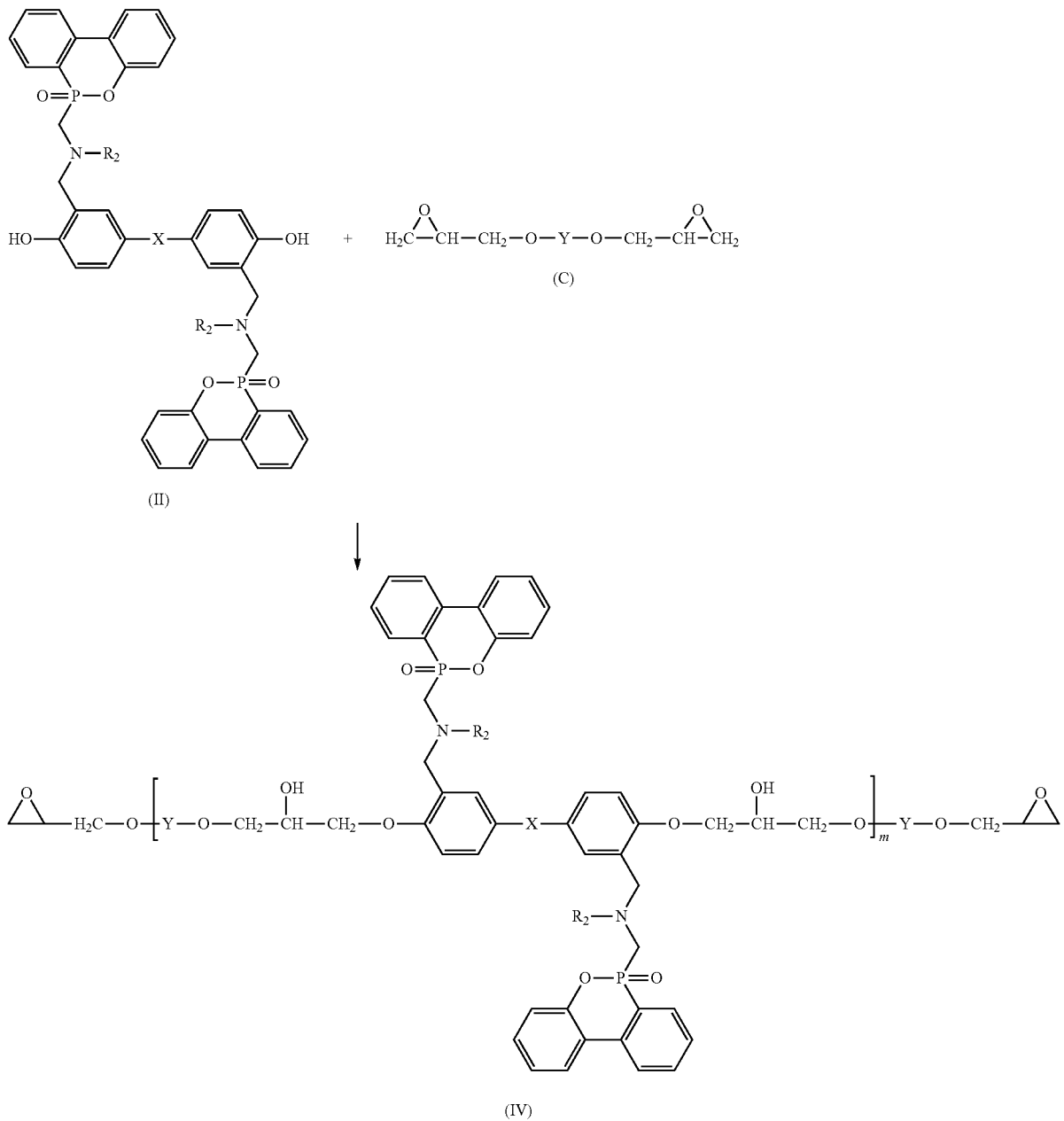

wherein, m is a number which is equal to or greater than 1 but less than or equal to 10, and Y is selected from the groups shown in embodiment 1.

According to one or more embodiments of the present disclosure, a phosphorus content of the advanced phosphorus-containing flame retardant epoxy resin (IV) is 0.5-4 wt %.

According to one or more embodiments of the present disclosure, a ratio of an epoxy group equivalent in the compound (C) to a phenolic equivalent in the phosphorus-containing bisphenols (II) is between 1:1 and 10:1.

Curing of the Advanced Phosphorus-Containing Flame Retardant Epoxy Resin (IV):

The advanced phosphorus-containing flame retardant epoxy resin (IV) can be cured through the curing agent as shown in embodiment 1, to form a phosphorus-containing flame retardant epoxy resin thermoset.

Synthesis Example 1-1

Preparation of a Phosphorus-Containing Bisphenol (I-a)

According to the structure of the phosphorus-containing bisphenol (I), a phosphorus-containing bisphenol (I-a) in which X is $CH_2$ can be synthesized, and has the following structure:

(I-a)

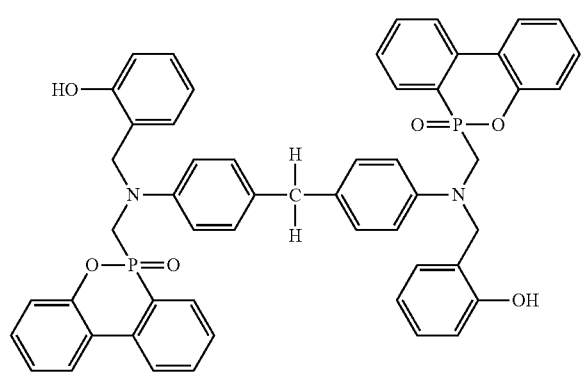

A synthetic method of the phosphorus-containing bisphenol (I-a) is as follows: 0.2 mol (86.9 g) of aromatic diamine 4,4'-diaminodiphenylmethan (DDM)-based benzoxazine resin P-d (commercialized benzoxazine resin P-d is available from Shikoku Chemicals Corporation) and 0.4 mol (86.46 g) of DOPO are added into a 500 ml single-neck round-bottom flask containing 200 ml of tetrahydrofuran (THF). AfterAfter they are reacted for 1 hour at room temperature and are dissolved completely, the temperature is increased to a reflux temperature and the reaction is maintained for 12 hours. After the reaction ends, they are directly poured into 1,000 ml of deionized water to be separated out and washed and then filtered by using an air suction filter after being washed into powder. The obtained filter cake is dried in a vacuum oven at 110° C., and the generated product is yellow powder, whose weight 164.7 g, yield is 95%, and melting point is 118° C. FIG. 1 is a $^1$H NMR spectrum of the phosphorus-containing bisphenol (I-a).

Synthesis Example 1-2

Preparation of a Phosphorus-Containing Bisphenol (I-b)

According to the structure of the phosphorus-containing bisphenol (I), a phosphorus-containing bisphenol (I-b) in which X is —O— can be synthesized, and has the following structure:

(I-b)

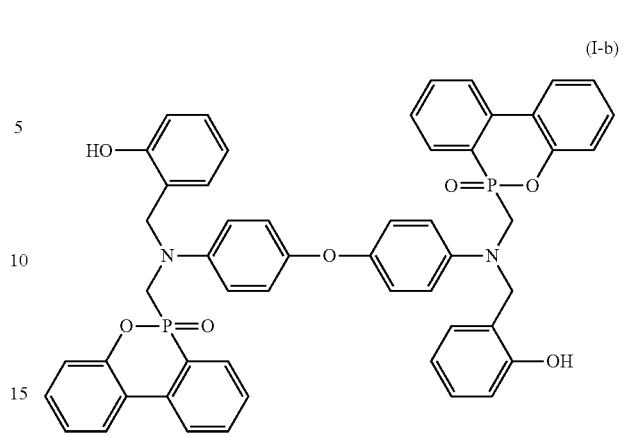

A synthetic method of the phosphorus-containing bisphenol (I-b) is as follows: by means of the steps as shown in synthesis example 1-1, the phosphorus-containing bisphenol (I-b) can be prepared by using 0.2 mol (87.3 g) of aromatic diamine 4,4-oxydianiline (ODA)-based benzoxazine resin ODABZ (commercialized benzoxazine resin ODABZ is available from Shikoku Chemicals Corporation) and 0.4 mol (86.46 g) of DOPO, and the generated product is yellow powder, whose weight is 166.7 g, yield is 95%, and melting point is 110° C.

Synthesis Example 1-3

An advanced phosphorus-containing flame retardant epoxy resin is synthesized by reacting the phosphorus-containing bisphenols (I-a) or (I-b) used as an epoxy resin modifier with diglycidyl ether of bisphenol A (DGEBA), diglycidyl ether of bisphenol F (DGEBF) or dicyclopentadiene epoxy.

The method of preparing advanced epoxy resins with different phosphorus contents is as follows: 10 g of epoxy resin (e.g. diglycidyl ether of bisphenol A, diglycidyl ether of bisphenol F or dicyclopentadiene epoxy) is added into a 100 n three-neck round-bottom flask with an outlet connected with nitrogen and an outlet connected with a condensing tube, and then is stirred by using a heating stirrer and heated to 150° C. in an oil bath pan. The required amount of phosphorus-containing bisphenol (I-a) is added into the above flask and reacted for 1.5 hours, thus obtaining a transparent viscous liquid. A liquid epoxy resin is obtained after cooling.

An advanced phosphorus-containing flame retardant epoxy resin (III-a) is synthesized by using the phosphorus-containing bisphenol (I-a) as an epoxy resin modifier, and has the following general formula:

(III-a)

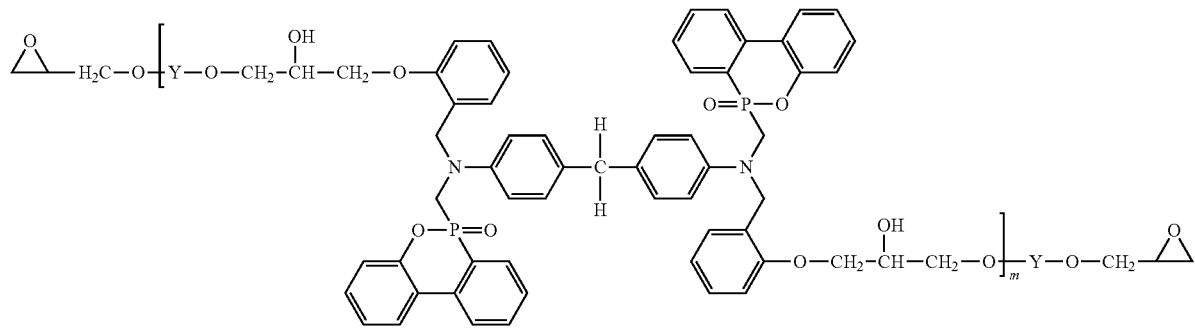

An advanced phosphorus-containing flame retardant epoxy resin (III-b) is synthesized by using phosphorus-containing bisphenol (I-b) as an epoxy resin modifier, and has the following general formula:

(III-b)

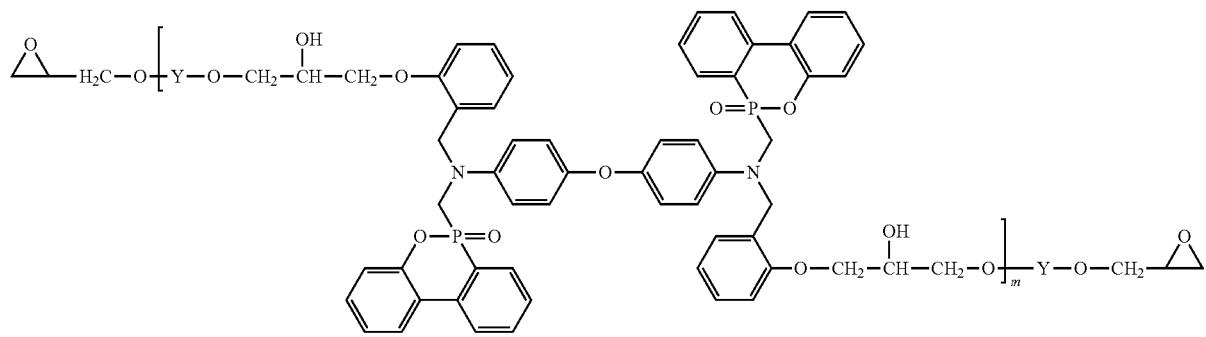

According to different reactants (phosphorus-containing bisphenol and epoxy resin) and different phosphorus contents of the products to be synthesized, some advanced phosphorus-containing flame retardant epoxy resins and phosphorus-containing flame retardant epoxy thermosets with different properties can be synthesized. The parameters of the reactants and the products are described in Table 1 below, and the properties of the epoxy thermosets are described in Table 2 below.

Synthesis Example 2-1

Preparation of a Phosphorus-Containing Bisphenol (II-a)

According to the structure of the phosphorus-containing bisphenol (II), a phosphorus-containing bisphenol (II-a) in which X is $CH_2$ can be synthesized, and has the following structure:

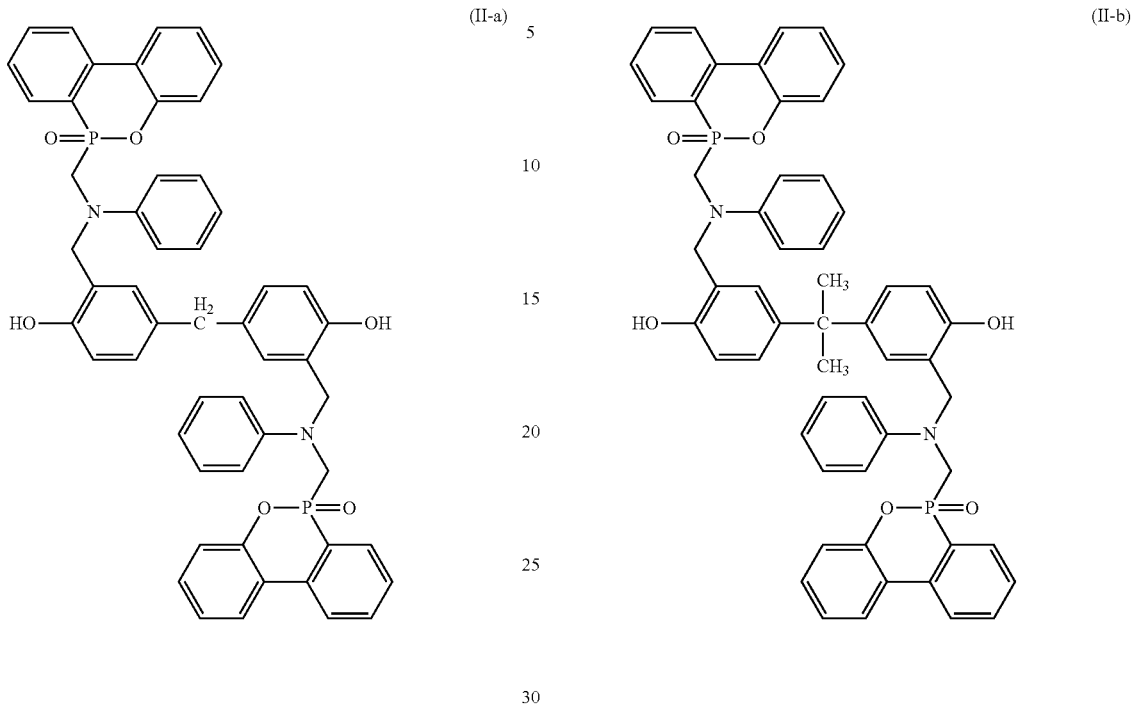

A synthetic method of the phosphorus-containing bisphenol (II-a) is as follows: by means of the same synthetic method of the phosphorus-containing bisphenols (I-a) as shown in embodiment 1, the phosphorus-containing bisphenols (II-a) can be synthesized by using 0.2 mol (86.9 g) of bisphenol-based bis(3,4-dihydro-2H-3-phenyl-1,3-benzoxazinyl) methane benzoxazine (e.g. commercialized benzoxazine resin F-a is available from Shikoku Chemicals Corporation) and 0.4 mol (86.46 g) of DOPO, and the generated product is yellow powder, whose weight is 162.9 g, yield is 94%, and melting point is 115° C.

Synthesis Example 2-2

Preparation of a Phosphorus-Containing Bisphenol (II-b)

According to the structure of the phosphorus-containing bisphenol (II), a phosphorus-containing bisphenol (II-b) in which X is —C(C$_2$H$_3$)$_2$— can be synthesized, and has the following structure:

A synthetic method of the phosphorus-containing bisphenol (II-b) is as follows: by means of the same synthetic method of the phosphorus-containing bisphenols (I-a) as shown in embodiment 1, the phosphorus-containing bisphenol (II-b) can be synthesized by using 0.2 mol (92.51 g) of bisphenol A-based benzoxazine resin (commercialized benzoxazine resin B-a is available from Shikoku Chemicals Corporation) and 0.4 mol (86.46 g) of DOPO, and the generated product is yellow powder, whose weight is 170.1 g, yield is 95%, and melting point is 118° C.

Synthesis Example 2-3

An advanced phosphorus-containing flame retardant epoxy resin can be synthesized by reacting the phosphorus-containing bisphenols (II-a) or (II-b) used as a epoxy resin modifier with diglycidyl ether of bisphenol A, diglycidyl ether of bisphenol F or dicyclopentadiene epoxy.

An advanced phosphorus-containing flame retardant epoxy resin (IV-a) is synthesized by using the phosphorus-containing bisphenol (II-a) as an epoxy resin modifier, and has the following general formula:

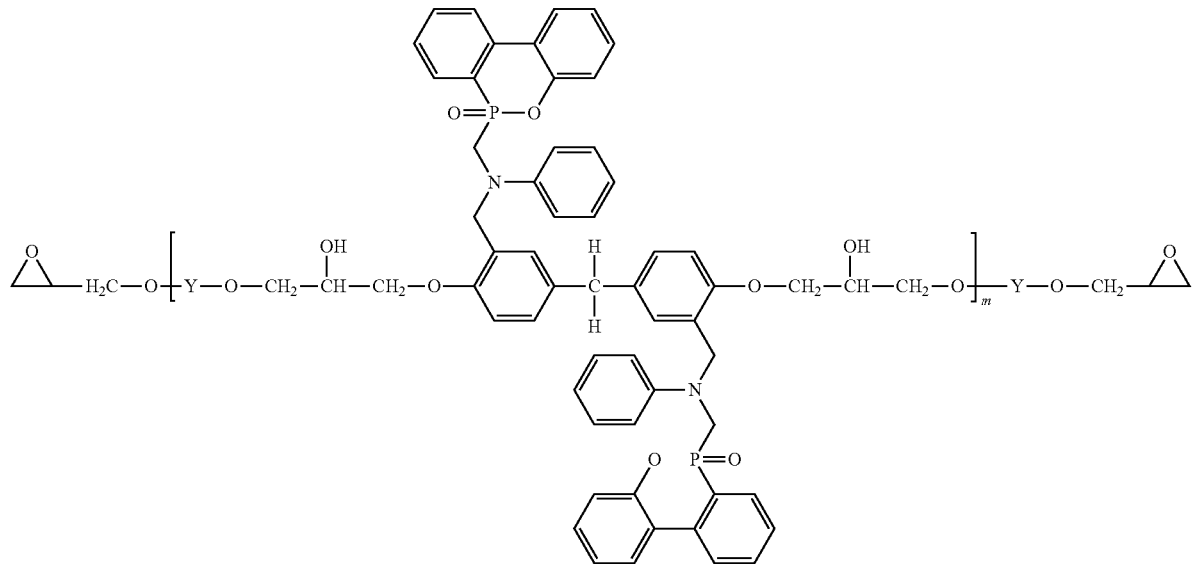

(IV-a)

An advanced phosphorus-containing flame retardant epoxy resin (IV-b) is synthesized by using phosphorus-containing bisphenol (II-b) as an epoxy resin modifier, and has the following general formula:

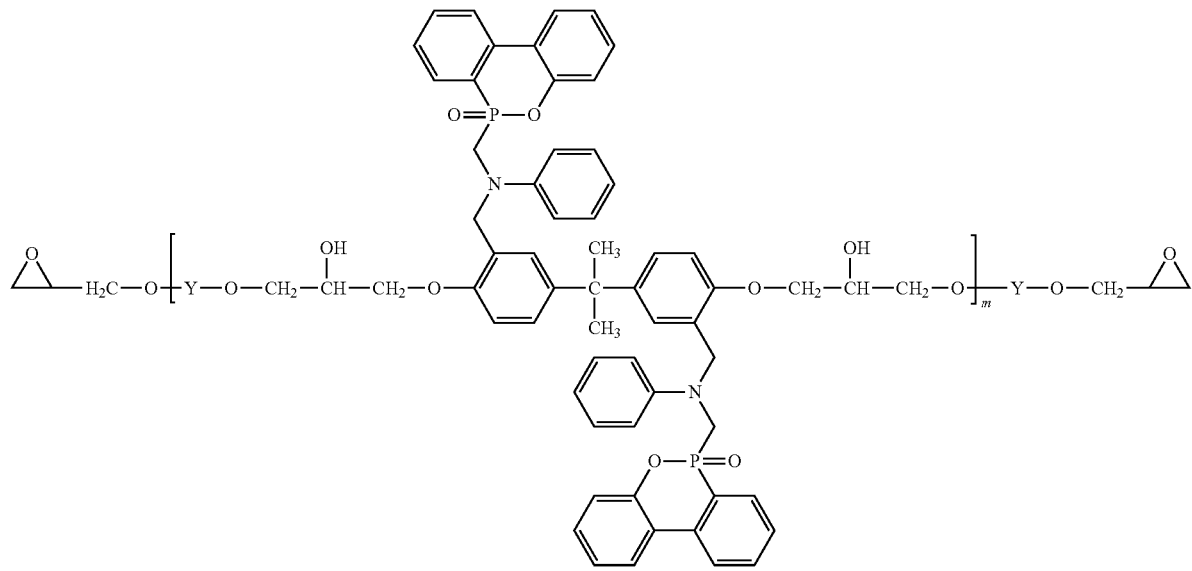

(IV-b)

According to different reactants (phosphorus-containing bisphenol and epoxy resin) and different phosphorus contents of the products to be synthesized, some advanced phosphorus-containing flame retardant epoxy resins and phosphorus-containing flame retardant epoxy thermosets with different properties can be synthesized. The parameters of the reactants and the products are described in Table 1, and the properties of the epoxy thermosets are described in Table 2.

TABLE 1

Preparing methods and results of advanced phosphorus-containing flame retardant epoxy resins

| Embodiments | Synthesis Examples | Phosphorus-containing bisphenols | Dose (g) | Epoxy resins | Dose (g) | Advanced epoxy resin NO. | Practical/theoretical epoxy equivalent (g/eq) | Phosphorus content (wt %) |
|---|---|---|---|---|---|---|---|---|
| Embodiment 1 | 1-3 | I-a | 1.63 | Y = —C₆H₄—C(CH₃)₂—C₆H₄— | 10 | III-aa-1.0 | 237/266 | 1.0 |
| | | | 2.65 | | 10 | III-aa-1.5 | 256/252 | 1.5 |
| | | | 3.88 | | 10 | III-aa-2.0 | 309/284 | 2.0 |
| | | | 5.37 | | 10 | III-aa-2.5 | 352/327 | 2.5 |
| | | | 2.65 | Y = —C₆H₄—CH₂—C₆H₄— | 10 | III-ab-1.5 | 253/248 | 1.5 |
| | | | 2.65 | Y = —C₆H₄—(dicyclopentadienyl)—C₆H₄— | 10 | III-ac-1.5 | 391/373 | 1.5 |
| | 1-3 | I-b | 2.66 | Y = —C₆H₄—C(CH₃)₂—C₆H₄— | 10 | III-ba-1.5 | 274/268 | 1.5 |
| | | | 2.65 | Y = —C₆H₄—CH₂—C₆H₄— | 10 | III-bb-1.5 | 259/248 | 1.5 |
| | | | 2.65 | Y = —C₆H₄—(dicyclopentadienyl)—C₆H₄— | 10 | III-bc-1.5 | 382/373 | 1.5 |
| Embodiment 2 | 2-3 | II-a | 2.65 | Y = —C₆H₄—C(CH₃)₂—C₆H₄— | 10 | IV-aa-1.5 | 263/252 | 1.5 |
| | | | 2.65 | Y = —C₆H₄—CH₂—C₆H₄— | 10 | IV-ab-1.5 | 258/248 | 1.5 |
| | | | 2.65 | Y = —C₆H₄—(dicyclopentadienyl)—C₆H₄— | 10 | IV-ac-1.5 | 388/373 | 1.5 |
| | 2-3 | II-b | 2.65 | Y = —C₆H₄—C(CH₃)₂—C₆H₄— | 10 | IV-ba-1.5 | 285/271 | 1.5 |
| | | | 2.65 | Y = —C₆H₄—CH₂—C₆H₄— | 10 | IV-bb-1.5 | 261/250 | 1.5 |

TABLE 1-continued

Preparing methods and results of advanced phosphorus-containing flame retardant epoxy resins

| Embodiments | Synthesis Examples | Reactants: Phosphorus-containing bisphenols | Dose (g) | Epoxy resins | Dose (g) | Advanced epoxy resin NO. | Practical/theoretical epoxy equivalent (g/eq) | Phosphorus content (wt %) |
|---|---|---|---|---|---|---|---|---|
| | | | 2.65 | Y = (structure) | 10 | IV-bc-1.5 | 391/379 | 1.5 |

Synthesis Example 3

Preparation of an Epoxy Thermoset

The advanced epoxy resin is heated to 150° C. into a molten state, and then a hardener 4,4'-diamino diphenyl sulfone (DDS) is added into the same equivalent of the above advanced epoxy resin and stirred, followed by curing in an oven at 180° C. for 2 hours, at 200° C. for 2 hours and at 220° C. for 2 hours in turn.

Table 2 is the analytical data on thermal properties of the thermosets in the embodiments of the present disclosure and the results of glass transition temperature (Tg) and UL-94 flammability testing of the resulting epoxy thermosets prepared by the above synthesis examples.

As can be known from Table 2, an inflammable epoxy resin (advanced diglycidyl ether of bisphenol A) can conform to UL-94 flammability testing V-0 and has perfect glass transition temperature when advancement reaction of phosphor-containing bisphenol of embodiments of the present disclosure with epoxy resin is carried out. For example, (III-aa-1.5)/DDS cured (phosphorus content: 1.23%) in synthesis example 1-3 may have a glass transition temperature up to 189° C.

Figure 2:
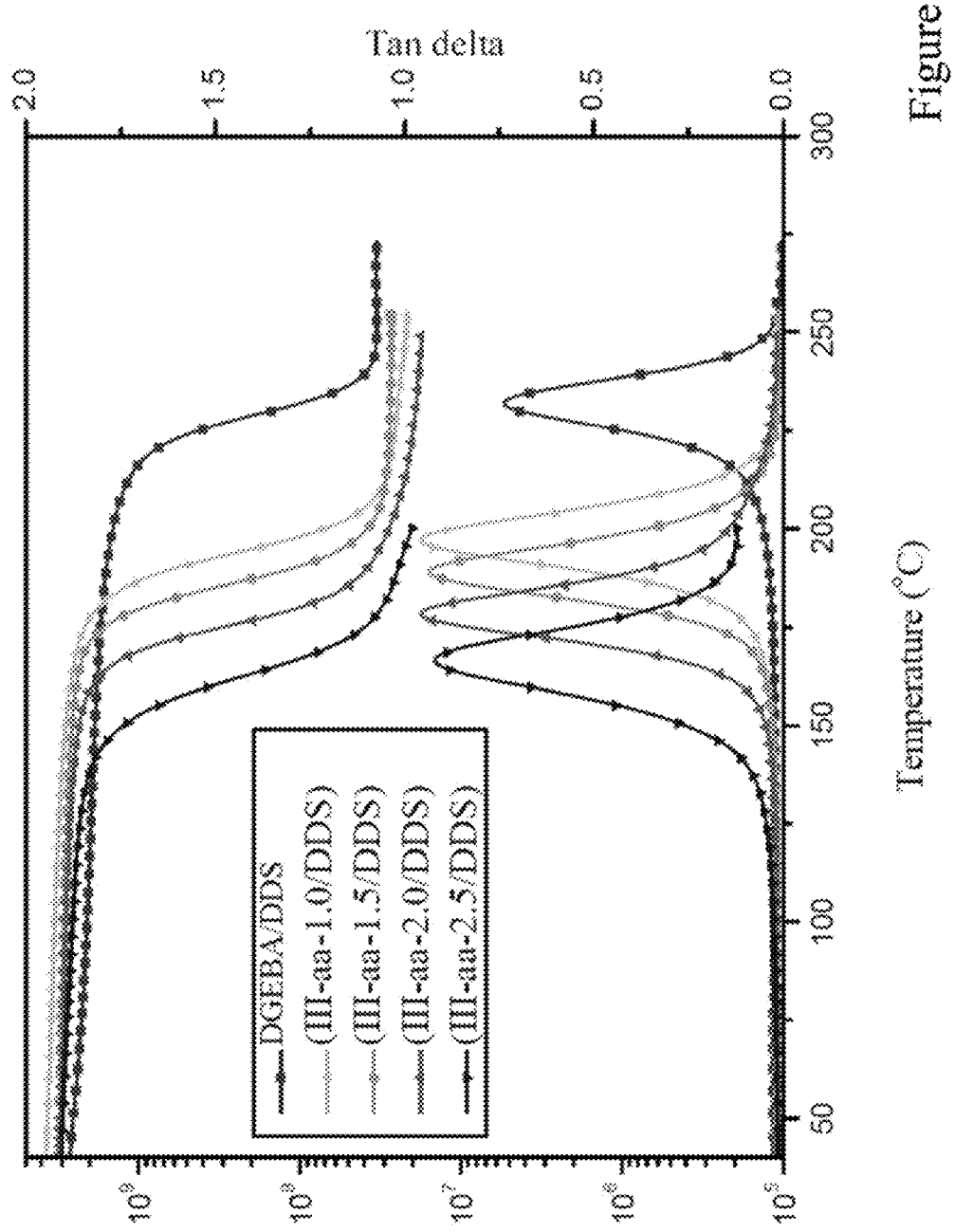
FIG. 2 is a dynamic mechanical property analysis diagram of a series of (III-aa)/DDS thermosets with different phosphorus contents.

FIG. 2 is a dynamic mechanical property analysis diagram of (III-aa-1.5)/DDS thermosets. The curves at the top of FIG. 2 are storage modulus of each sample (corresponding to the vertical axis on the left of the figure), which means the allowable stress of each sample under different temperatures. The wave crests at the bottom of FIG. 2 are softening glass transition temperatures of each sample (corresponding to the vertical axis on the right of the figure), which means the softening temperature of each sample. A higher temperature indicates a higher operating temperature.

As can be known from FIG. 2, the phosphorus-containing flame retardant epoxy resins in the embodiments of the present disclosure have proper glass transition temperatures and can be operated at a high temperature of 150-200° C. Moreover, the storage moduli of the modified epoxy resins are higher than those of the unmodified epoxy resins. For example, the storage modulus (3.1 GPa) of (III-aa-1.5)/DDS cured at 50° C. is higher than that (2.5 GPa) of unmodified diglycidyl ether of bisphenol A/DDS cured. The curves of FIG. 2 indicate that, comparing with the unmodified epoxy thermoset (diglycidyl ether of bisphenol A/DDS), the epoxy thermoset (III-aa-1.5)/DDS modified by adding a phosphor has a good mechanical property though its maximum bearing capacity decreases slightly at a high temperature. Therefore,

TABLE 2

Analytical data on thermal properties of thermosets

| | Synthesis Examples | Advanced epoxy resin/curing agent | Phosphorus content (wt %) | Hydrogen content (wt %) | Glass transition temperature (Tg, ° C.) | UL-94 level of testing |
|---|---|---|---|---|---|---|
| Comparison Example | — | Diglycidyl ether of bisphenol A/DDS | 0 | 2.09 | 232 | Combustion |
| Embodiment 1 | 1-3 | (III-aa-1.0)/DDS | 0.79 | 2.69 | 198 | V-1 |
| | | (III-aa-1.5)/DDS | 1.23 | 2.56 | 189 | V-0 |
| | | (III-aa-2.0)/DDS | 1.70 | 2.63 | 178 | V-0 |
| | | (III-aa-2.5)/DDS | 2.12 | 2.65 | 169 | V-0 |
| | | (III-ab-1.5)/DDS | 1.23 | 2.56 | 181 | V-0 |
| | | (III-ac-1.5)/DDS | 1.23 | 2.56 | 185 | V-1 |
| | 1-3 | (III-ba-1.5)/DDS | 1.23 | 2.56 | 178 | V-0 |
| | | (III-bb-1.5)/DDS | 1.23 | 2.56 | 169 | V-0 |
| | | (III-bc-1.5)/DDS | 1.23 | 2.56 | 173 | V-1 |
| Embodiment 2 | 2-3 | (IV-aa-1.5)/DDS | 1.23 | 2.56 | 181 | V-0 |
| | | (IV-ab-1.5)/DDS | 1.23 | 2.56 | 174 | V-0 |
| | | (IV-ac-1.5)/DDS | 1.23 | 2.56 | 178 | V-1 |
| | 2-3 | (IV-ba-1.5)/DDS | 1.23 | 2.56 | 185 | V-0 |
| | | (IV-bb-1.5)/DDS | 1.23 | 2.56 | 180 | V-0 |
| | | (IV-bc-1.5)/DDS | 1.23 | 2.56 | 183 | V-1 | it is more important to reduce the inflammability of benzoxazine resin by adding a phosphor element upon the mechanical property.

FIG. 3 is a thermogravimetric analysis diagram of (III-aa)/DDS cured with different phosphorus content. The residual ratio of the compounds in FIG. 3 at a high temperature indicates that the phosphorus-containing flame retardant epoxy resins in the embodiments of the present disclosure have a good thermostability and stable property below 350° C. Moreover, as the phosphorus content of the compound itself becomes higher, the residual ratio is higher. However, the residual ratio of unmodified diglycidyl ether of bisphenol A/DDS cured (phosphor-free) at a high temperature is obviously lower than that of phosphorus-containing flame retardant epoxy resin of the present disclosure FIG. 3 indicates that adding phosphor element really can help to provide thermostability and can also protect resin molecule from decomposing during heating.

According to the above description, it can be known that the phosphorus-containing flame retardant epoxy resins in the embodiments of the present disclosure are useful as circuit board materials and semiconductor packaging materials requiring a flame retardant property and can be used in other relevant fields.

Although the present disclosure has been disclosed with reference to the above embodiments, these embodiments are not intended to limit the present disclosure. It will be apparent to those skilled in the art that various modifications and variations can be made without departing from the scope or spirit of the present disclosure. Therefore, the scope of the present disclosure shall be defined by the appended claims.

What is claimed is:

1. A phosphorus containing bisphenol (I), comprising a structure as shown in the following formula:

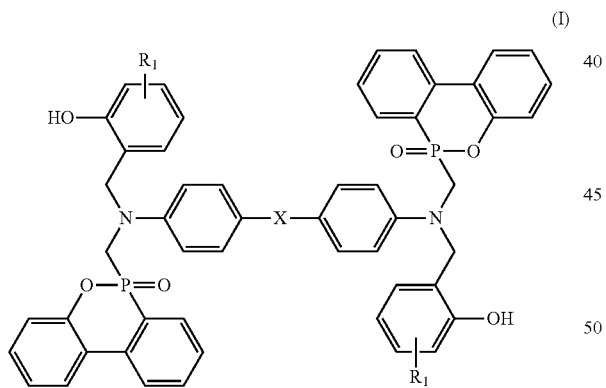

wherein, $R_1$ is selected from the following groups:

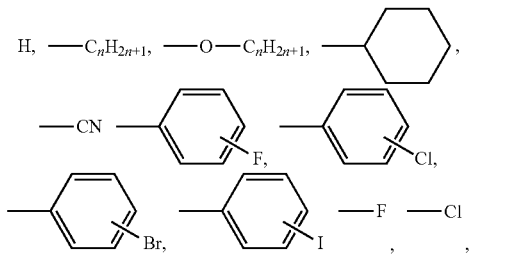

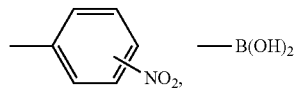

and X is selected from the following structures:

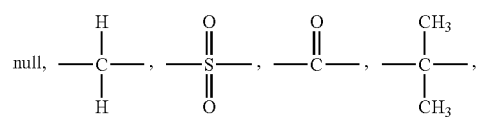

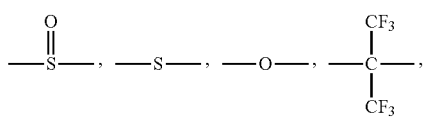

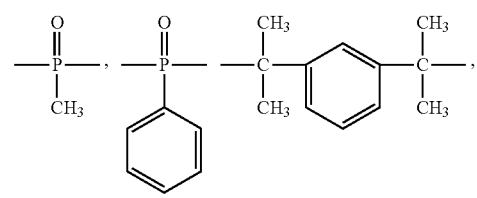

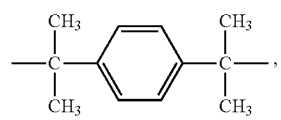

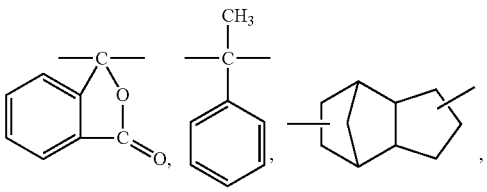

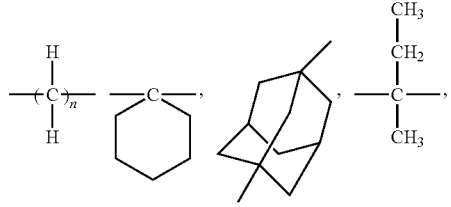

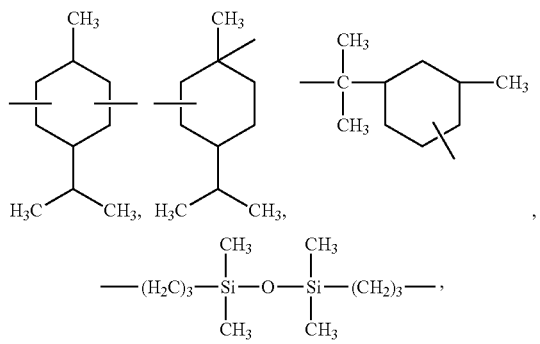

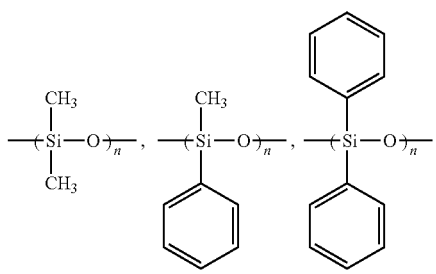
wherein, n is an integer which is equal to or greater than 1 but less than or equal to 10.
2. A phosphorus-containing bisphenol (II), comprising a structure as shown in the following formula:
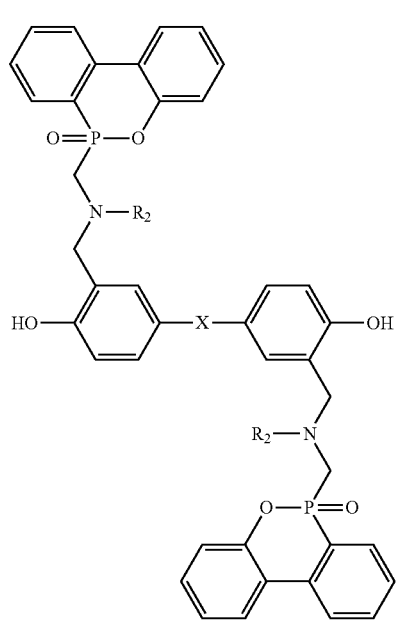
(II)
wherein, $R_2$ is selected from the following groups:
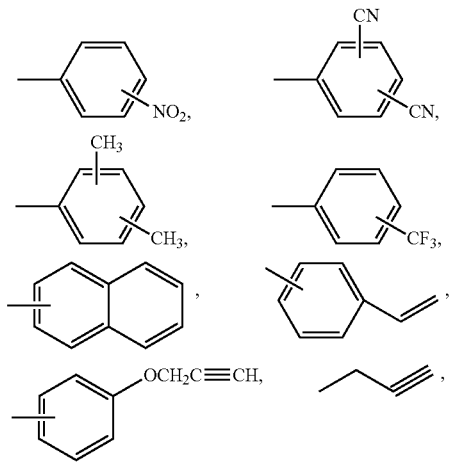
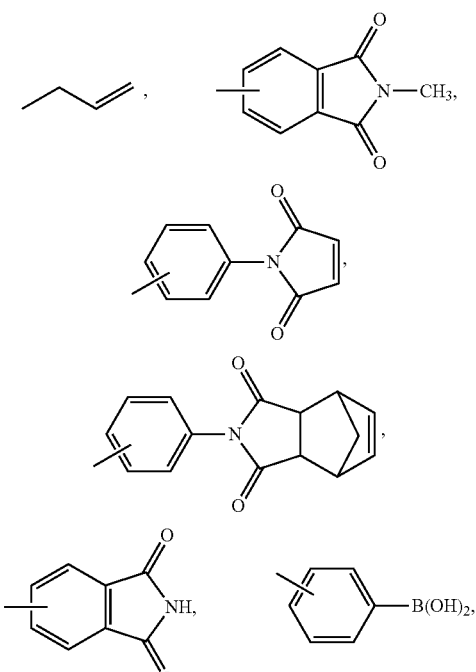
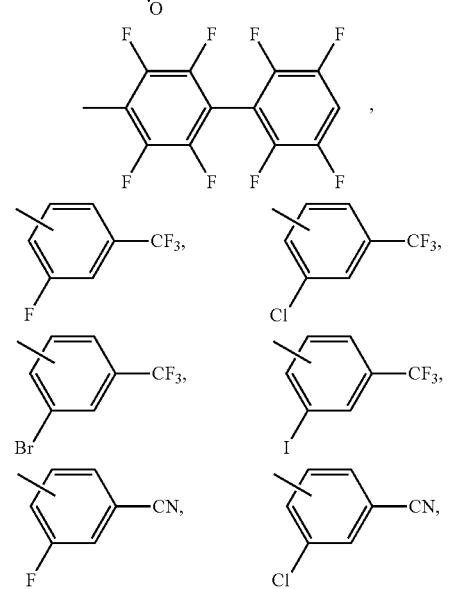

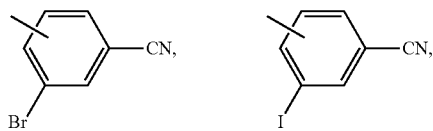
and X is selected from the following structures:
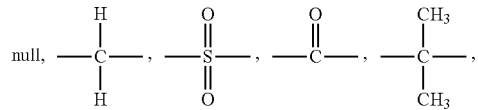
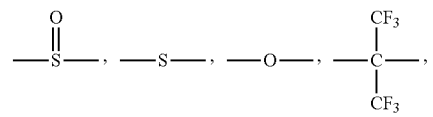
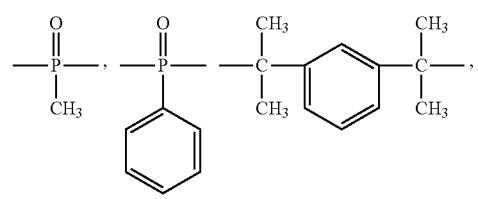
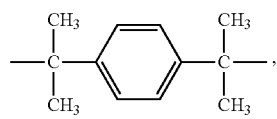
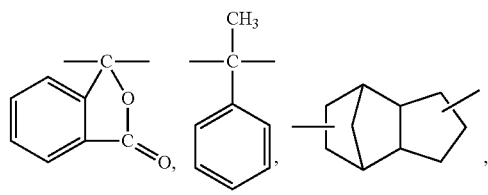
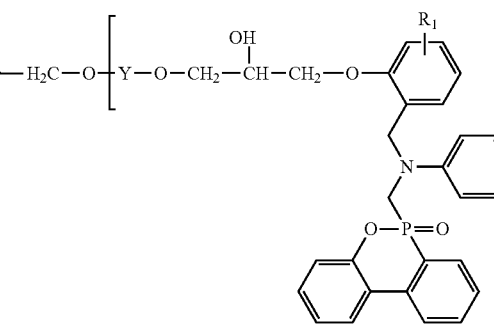
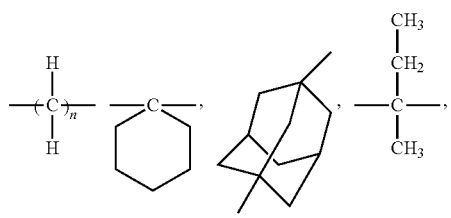
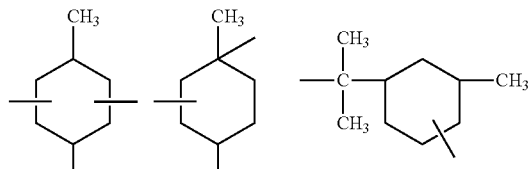
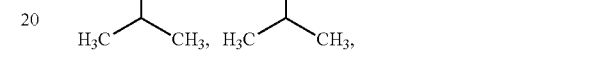
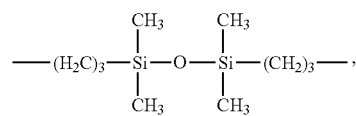
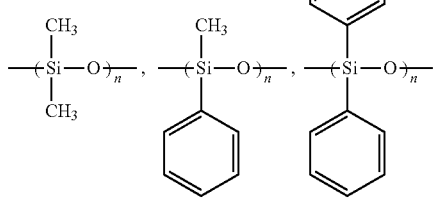
wherein n is an integer which is equal to or greater than 1 but less than or equal to 10.
3. An advanced phosphorus-containing flame retardant epoxy resin (III), derived from the phosphorus-containing bisphenol (I) of claim 1, comprising a structure as shown in the following formula:
(III)
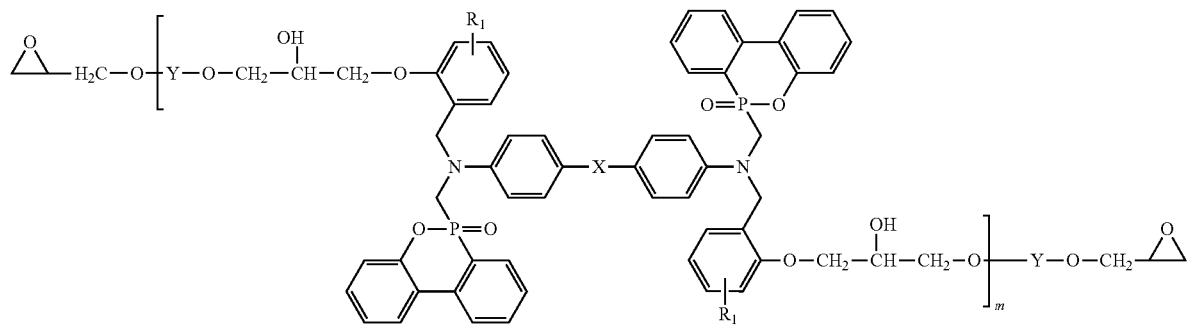

wherein, Y is selected from the following groups:
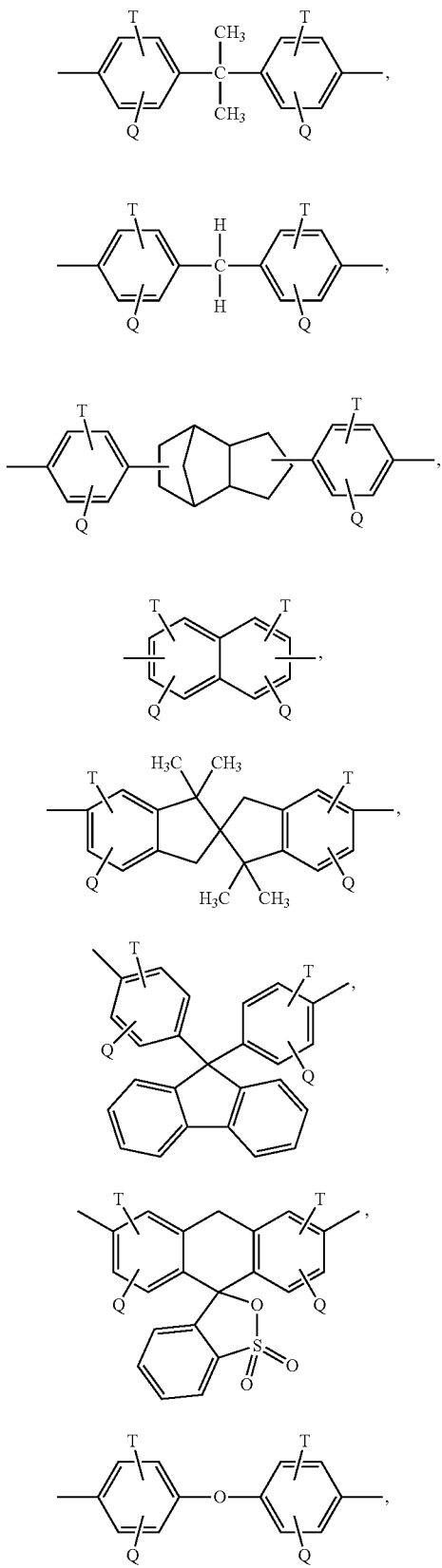
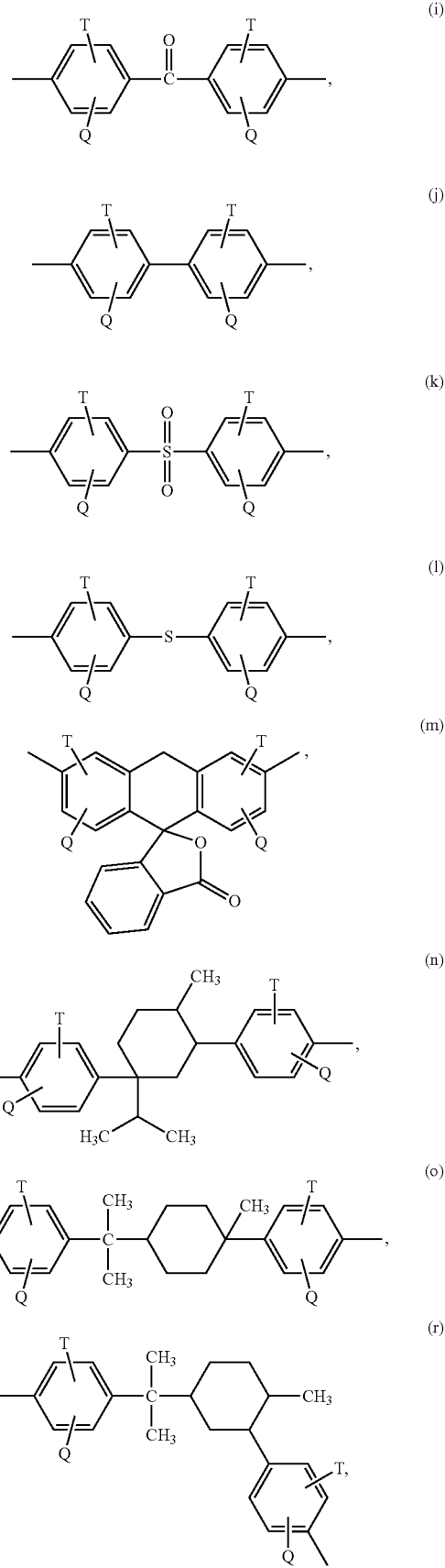

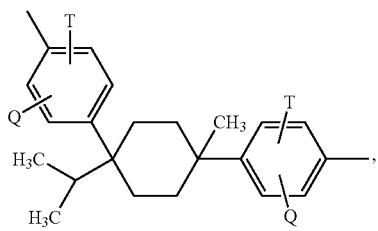

wherein, m is a number which is equal to or greater than but less than or equal to 10, and T and Q are respectively selected from a group consisting of hydrogen, $C_1$-$C_6$ alkyl, $CF_3$, phenyl and halogen.

4. An advanced phosphorus containing flame retardant epoxy resin (IV), derived from the phosphorus-containing bisphenol (II) of claim 2, comprising a structure as shown in the following formula:

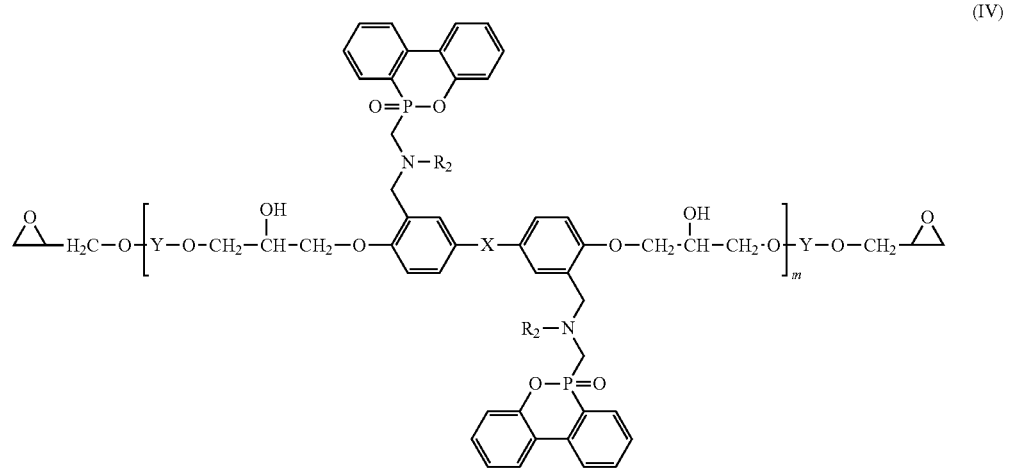

wherein, is selected from the following groups:

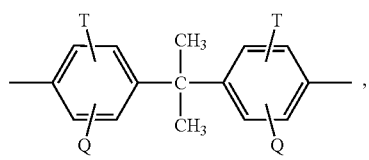

(a)

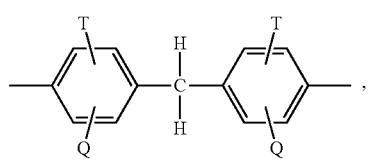

(b)

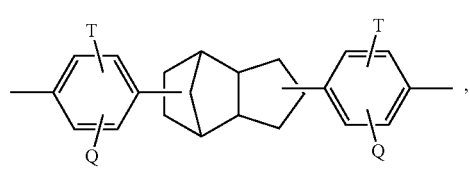

(c)

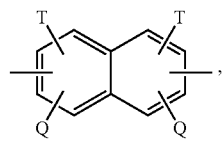

(d)

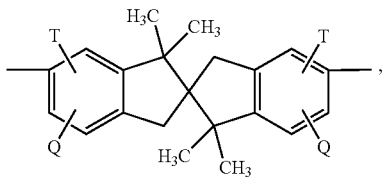

(e)

-continued

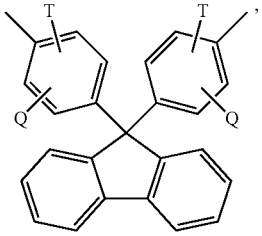

(f)

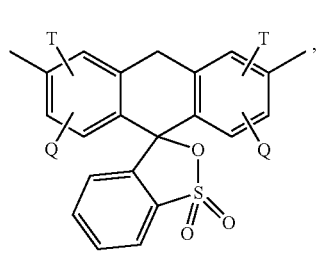

(g)

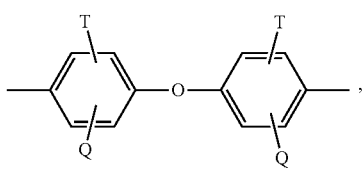
(h)

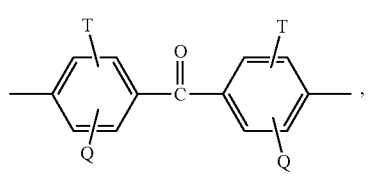
(i)

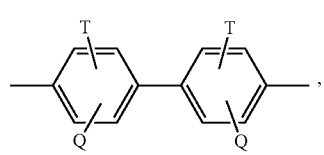
(j)

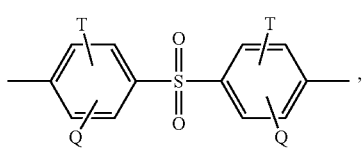
(k)

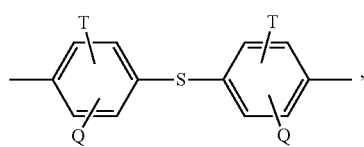
(l)

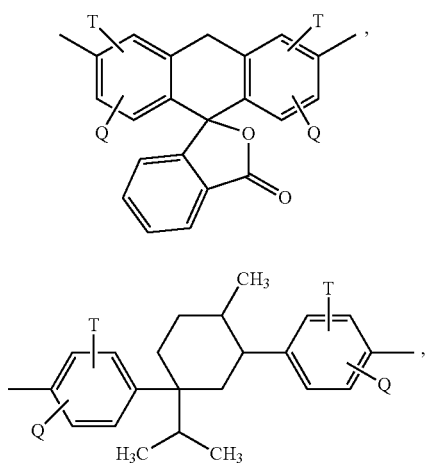
(m)

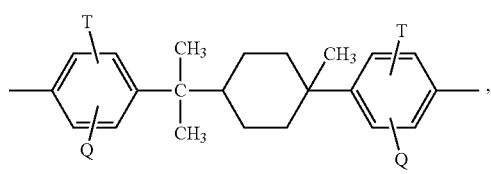
(n)

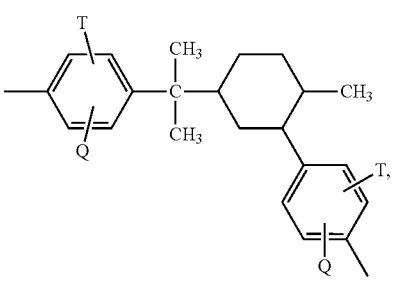
(r)

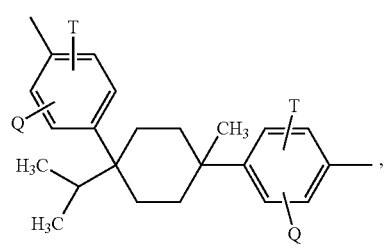
(s)

wherein, m is a number which is equal to or greater than 1 but less than or equal to 10, and T and Q are respectively selected from a group consisting of hydrogen, $C_1$-$C_6$ alkyl, $CF_3$, phenyl and halogen.

5. A method of preparing a phosphorus-containing flame retardant epoxy resin, comprising:

reacting a phosphorus-containing b phenol with a compound (C) having an epoxy group for a chain extension reaction, to form an advanced phosphorus-containing flame retardant epoxy resin;

wherein the phosphorus-containing bisphenol is prepared by reacting a phosphorus-containing compound (DOPO) with a benzoxazine monomer, the phosphorus-containing compound (DOPO) has a structure as shown in the following formula:

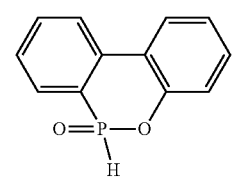
(DOPO)

the benzoxazine monomer has a structure as shown in a monomer (A) or a monomer (B):

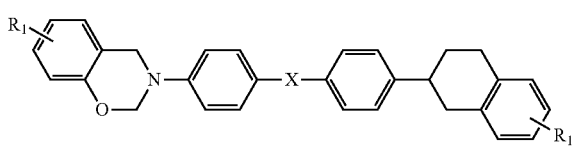
(A)

-continued
(B) 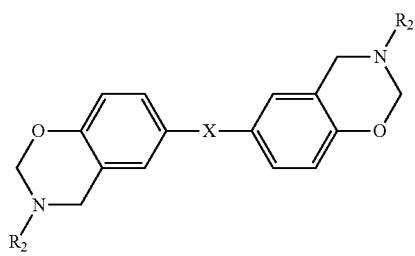
R₁ is selected from the following groups:
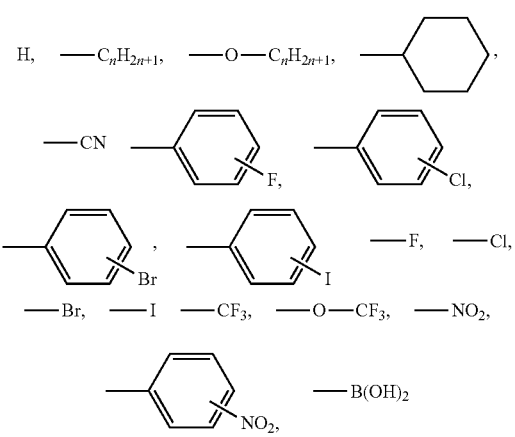
R₂ is selected from the following groups:
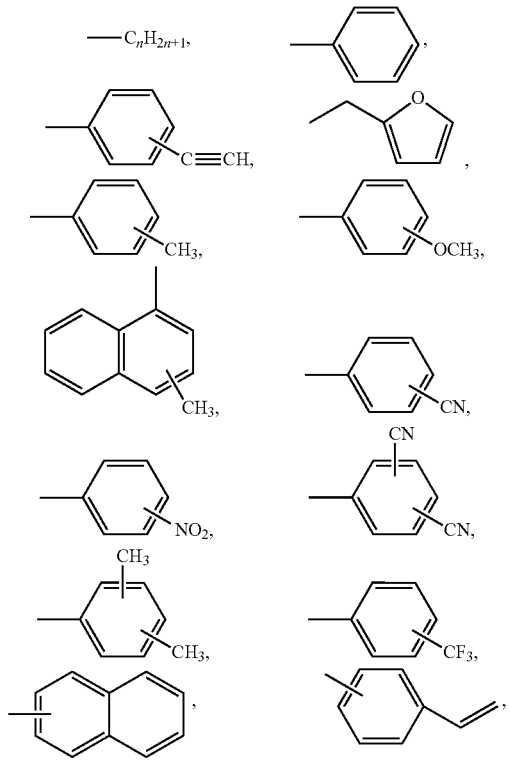
-continued
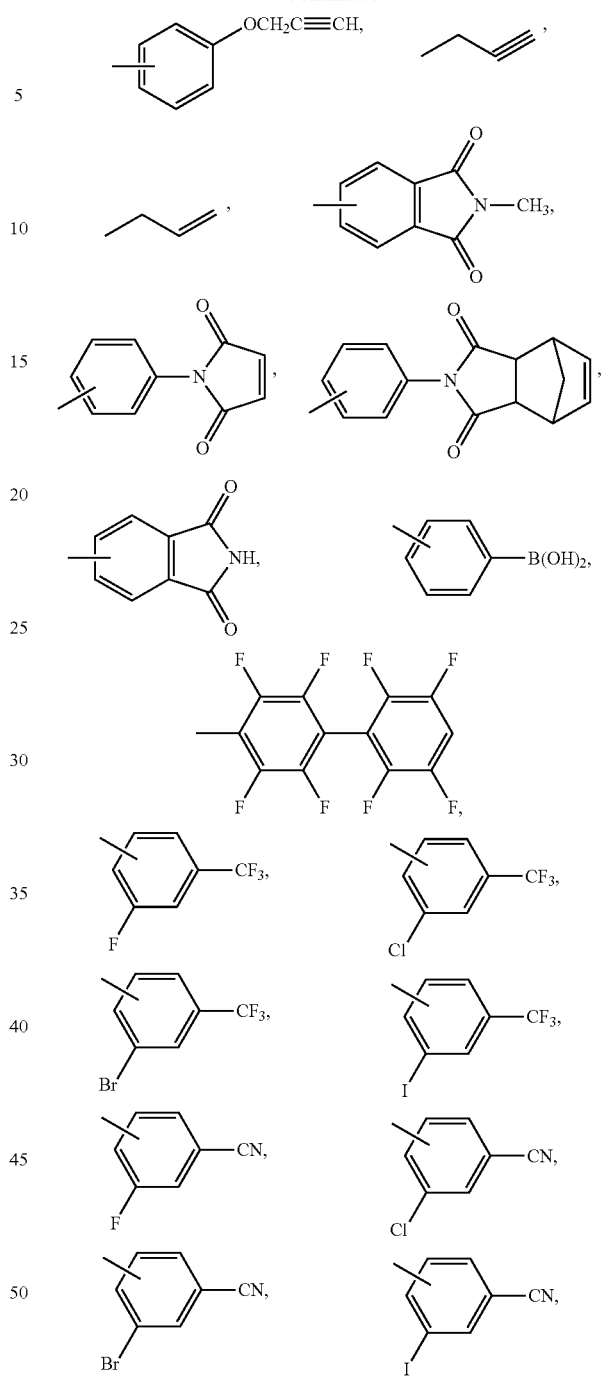
X is selected from the following structures:
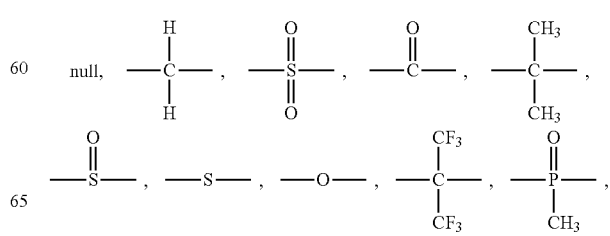

-continued
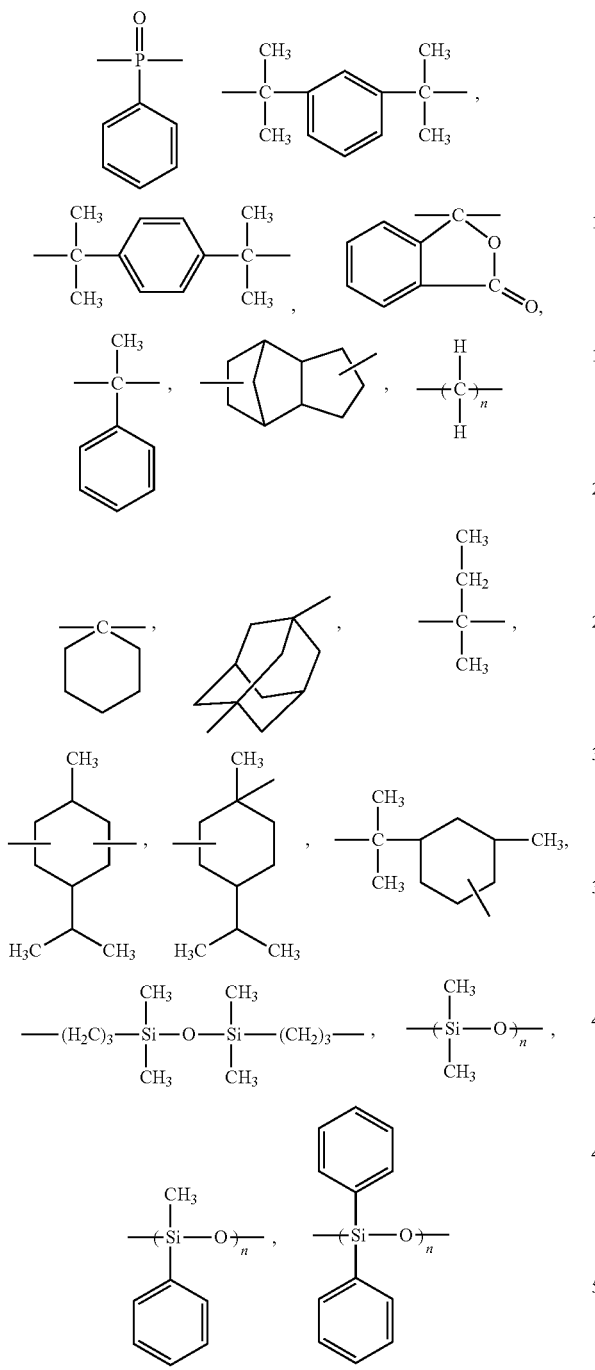
and n is an integer which is equal to or greater than 1 but less than or equal to 10;
wherein the compound (C) has a structure as shown in the following formula:
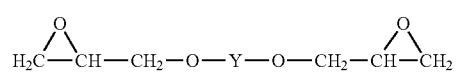
(C)
wherein, Y is selected from the following groups:
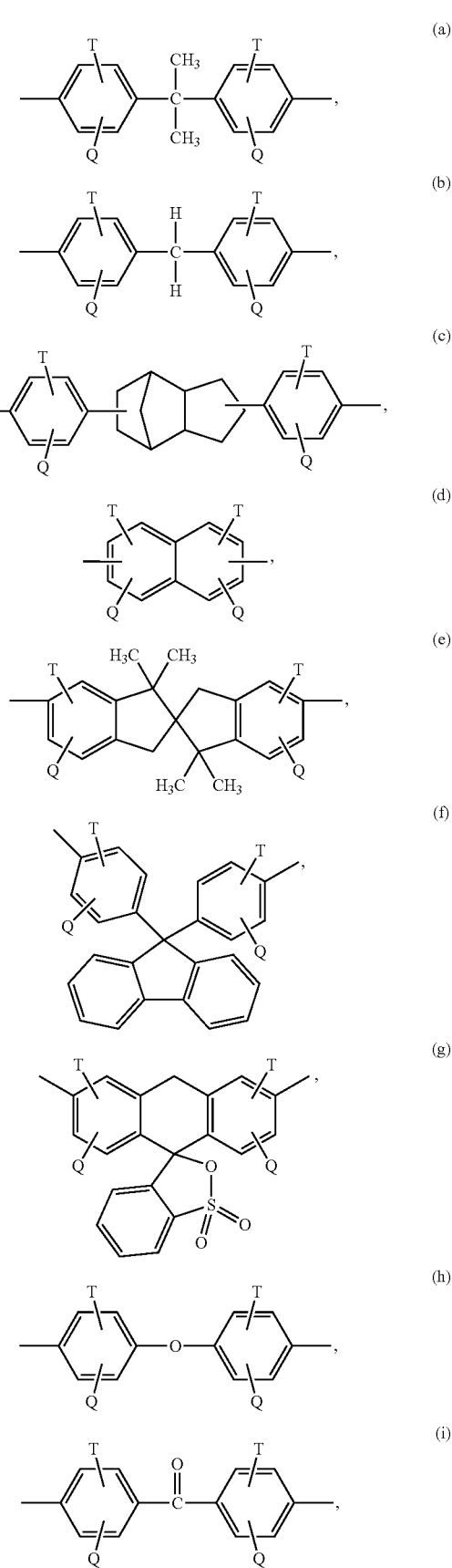

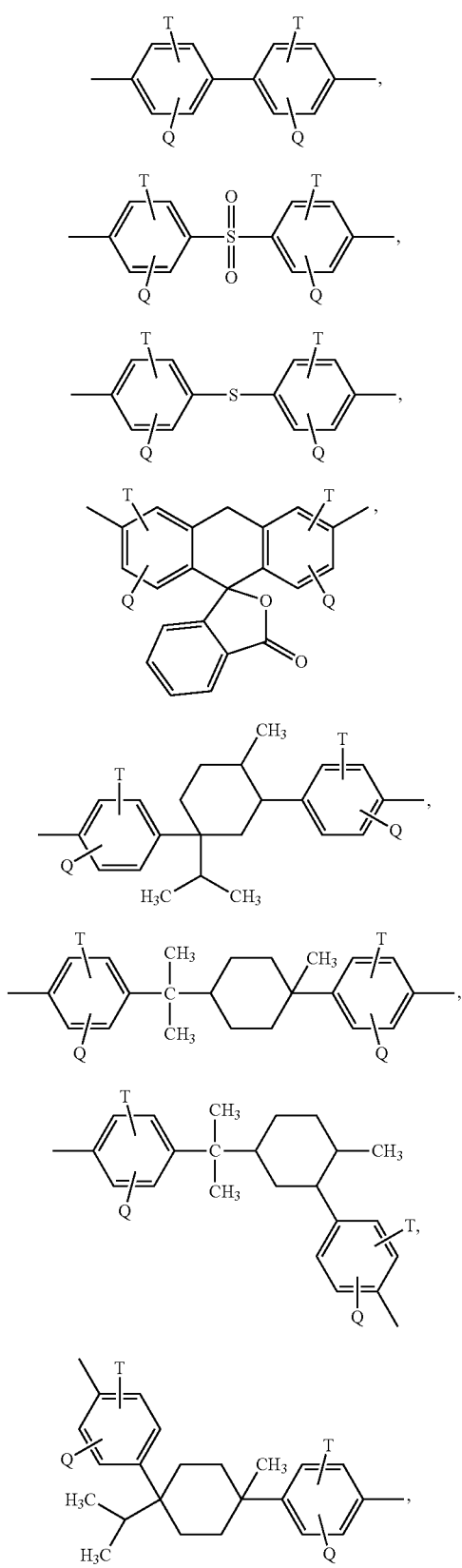

and T and Q are respectively selected from a group consisting of hydrogen, $C_1$-$C_6$ alkyl, $CF_3$, phenyl and halogen.

6. The method of claim 5, wherein the chain extension reaction is carried out at 100-200° C. without adding a catalyst.

7. The method of claim 5, wherein the chain extension reaction is carried out at 100-200° C. with a catalyst, and the catalyst is selected from the group consisting of phenylimidazole, dimethyl midazole, triphenylphosphine, quaternary phosphorus compound and quaternary ammonium compound.

8. The method claim 5, wherein a phosphorus content of the advanced phosphorus-containing flame retardant epoxy resin is 0.5-4 wt %.

9. The method of claim 5, wherein a ratio of an epoxy group equivalent in the compound (C) to a phenolic equivalent in the phosphorus-containing bisphenol is between 1:1 and 10:1.

10. The method of preparing a phosphorus-containing flame retardant epoxy resin of claim 5, wherein the phosphorus-containing bisphenol has a structure as shown in the following formula (I-a):

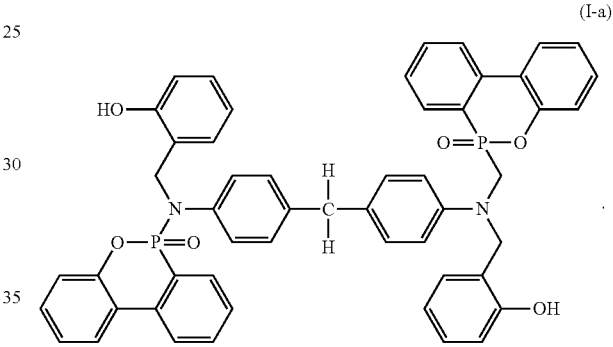

(I-a)

11. The method of claim 10, wherein the phosphorus-containing bisphenol (I-a) is reacted with the compound (C) for a chain extension reaction, and Y in the compound (C) is selected from the following (a), (b) and (c):

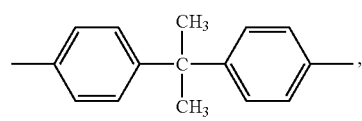

(a)

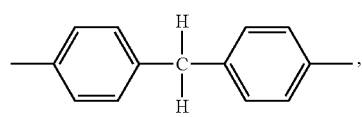

(b)

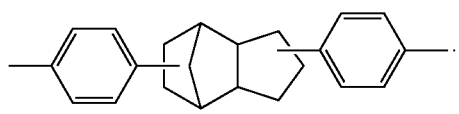

(c)

12. The method of claim 5, wherein the phosphorus-containing bisphenol has a structure as shown in the following formula (I-b):

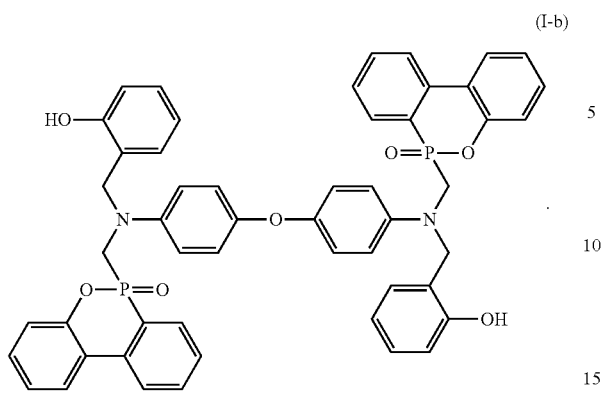
(I-b)

13. The method of claim 12, wherein the phosphorus-containing bisphenol (I-b) is reacted with the compound (C) for a chain extension reaction, and Y in the compound (C) is selected from the following (a), (b) and (c):

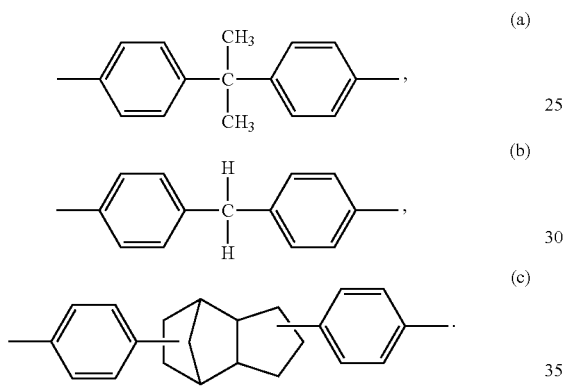

14. The method of claim 5, wherein the phosphorus-containing bisphenol (II-a) has the following structure:

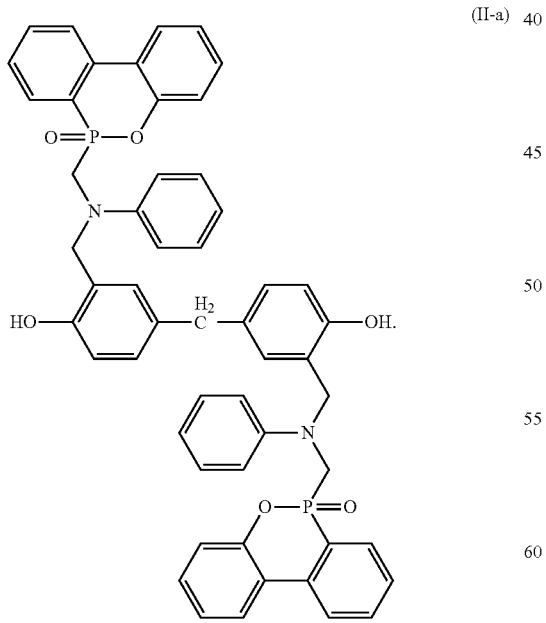
(II-a)

15. The method of claim 14, wherein the phosphorus-containing bisphenol (II-a) is reacted with the compound (C) for a chain extension reaction, and Y in the compound (C) is selected from the following (a), (b) and (c):

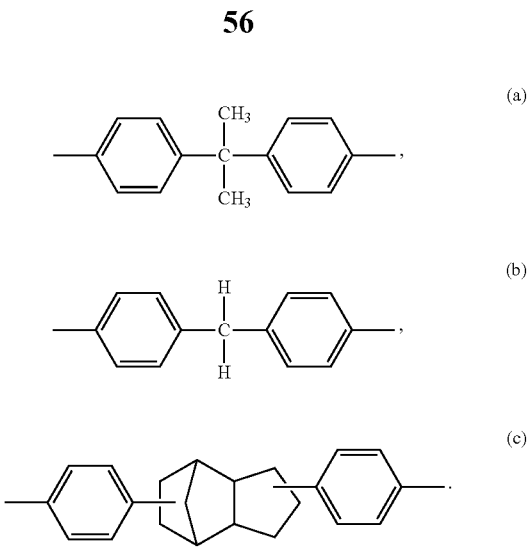

16. The method of claim 5, wherein the phosphorus-containing bisphenol (II-b) has the following structure:

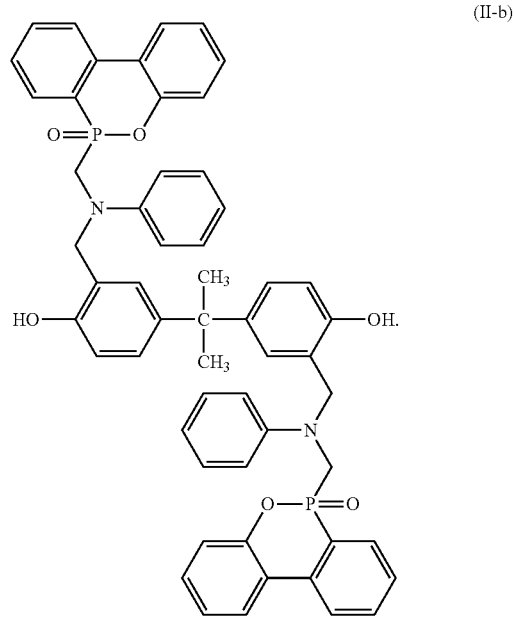 [SMILES: CC(C)(c1ccc(O)c(CN(CP2(=O)Oc3ccccc3-c3ccccc32)c2ccccc2)c1)c1ccc(O)c(CN(CP2(=O)Oc3ccccc3-c3ccccc32)c2ccccc2)c1]
(II-b)

17. The method of claim 16, wherein the phosphorus-containing bisphenol (II-b) is reacted it the compound (C) for a chain extension reaction, and Y in the compound (C) is selected from the following (a), (b) and (c):

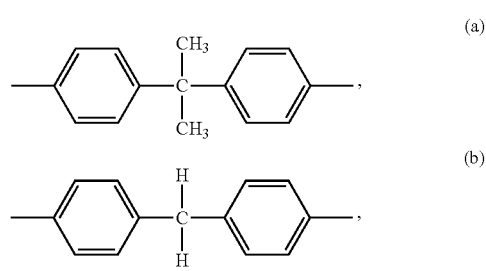

-continued

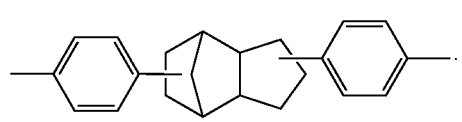 (c)

18. The claim 5, further comprising: curing the advanced phosphorus-containing flame retardant epoxy resin by using a curing agent, so as to form a phosphorus-containing flame retardant epoxy thermoset.

19. The method of claim 18, wherein the curing agent is phenol novolac resin, dicyandiamide, diaminodiphenyl methane, diaminodiphenyl sulfone, phthalic anhydride or hexahydrophthalic anhydride.

* * * * *